US005827830A

United States Patent [19]
Nudelman et al.

[11] Patent Number: 5,827,830
[45] Date of Patent: Oct. 27, 1998

[54] PLASMALOPSYCHOSINES AND PLASMALOCEREBROSIDES

[75] Inventors: Edward Nudelman, Seattle; Sen-Itiroh Hakomori, Mercer Island; Steven B. Levery; Yasuyuki Igarashi, both of Seattle, all of Wash.; Khalid Sadozai, Pakistan, Pakistan

[73] Assignee: The Biomembrane Intstitute, Seattle, Wash.

[*] Notice: The term of this patent shall not extend beyond the expiration date of Pat. No. 5,693,620.

[21] Appl. No.: 711,100

[22] Filed: Sep. 9, 1996

Related U.S. Application Data

[60] Division of Ser. No. 355,276, Dec. 12, 1994, Pat. No. 5,693,620, which is a continuation-in-part of Ser. No. 79,544, Jun. 22, 1993, abandoned, which is a continuation of Ser. No. 738,375, Jul. 31, 1991, abandoned.

[51] Int. Cl.$^6$ .............................. A61K 31/70; C07H 15/00
[52] U.S. Cl. .............................................. 514/25; 536/17.9
[58] Field of Search ............................... 514/25; 536/17.9

[56] References Cited

U.S. PATENT DOCUMENTS

| | | | |
|---|---|---|---|
| 4,284,763 | 8/1981 | Thelwall et al. | 536/120 |
| 4,544,552 | 10/1985 | Fraefel et al. | 514/23 |

OTHER PUBLICATIONS

J.C. Samson, "Gangliosides (Cronassial) as therapeutic agents in peripheral neuropathies" *Drugs of Today* (1986) 22: No. 2 pp. 73–107.

G. Zubay, *Biochemistry* (1983) pp. 581–583.

A. Veinberg et al., "Selective Protection of Hydroxyl Groups . . . " *Chemical Abstracts* (1971) 74: 54148a.

C.E. Ballou & A. Dell, "Polysaccharide–Lipid Interaction Analyzed by Fast–atom bombardment Mass Spectometry" *Carbohydrate Research* (1985) 140: 131–143.

L.G. Bennett & C.T. Bishop, "Structure of the Type XXVII Streptococcus . . . " *Can J. Chem.* (1977) 55: 8–16.

H. Björndal et al., "Gas–Liquid Chromatography and Mass Spectrometry . . . Polysaccharides" *Angew. Chem. Intl. Ed. Eng.* (1970) 9: 610–619.

I. Ciucanu & F. Kerek, "A Simple and Rapid Method for Permethylation of Carbohydrates" *Carbohydrate Research* (1984) 131: 209–217.

E.J. Corey & G. Schmidt, "Useful Procedures for the Oxidation of Alcohols Involving . . . Media" *Tetrahedron Lett.* (1979) 5: 399–402.

B. Domon & C.E. Costello, "Structure Elucidation of Glycosphingolipids and Gangliosides . . . Spectrometry" *Biochemistry* (1988) 27: 1534–1543.

J. Folch et al., "Isolation of Brian Strandin, A New Type of Large Molecule Tissue Component" *J. Biol. Chem.* (1951) 191: 819–831.

I. Fujii et al., "An Easy and Powerful Technique of Negative Ion Fast . . . Matrix" *J. Soc. Chem. Commun.* (1985) pp. 405–406.

(List continued on next page.)

*Primary Examiner*—Kathleen K. Fonda
*Attorney, Agent, or Firm*—Sughrue, Mion, Zinn, Macpeak & Seas, PLLC

[57] ABSTRACT

An isolated plasmalopsychosine selected from the group consisting of compound A and compound B:

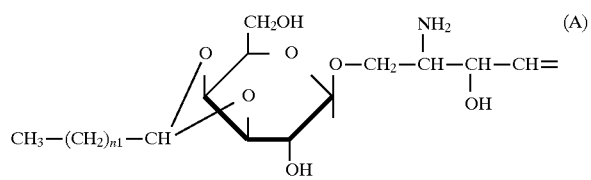

wherein n1 is 0–50 or an isolated synthetic plasmalocerebroside selected from the group consisting of compound C and compound D:

wherein n2 and n3 each is 0–50.

10 Claims, 21 Drawing Sheets

OTHER PUBLICATIONS

P.A. Gorin & T. Ishikawa, "Configuration of Pyruvic Acid Ketals, 4,6–0–Linked to D–galactose Units . . . Polysaccharides" *Can J. Chem.* (1967) 45: 521–532.

Y.A. Hannun & R.M. Bell, "Lysosphingolipids Inhibit Protein Kinase C: Implications for the Sphingolipidoses", *Science* (1987) 235: 670–674.

Y.A. Hannun & R.M. Bell, "Functions of Sphingolipid and Sphingolipids Breakdown Products in Cellular Regulation", *Science* (1989) 243: 500–507.

A. Hara & T. Taketomi, "Chemical Properties and Steroisomerism of Heterogeneous . . . Spectroscopy" *J. Biochem.* (Tokyo) (1986) 100: 415–423.

M.E. Hemling et al., "Fast Atom Bombardment Mass Spectrometry of . . . Sugars", *Biochemistry* (1984) 23: 5706–5713.

S. Hirase, "Studies on the Chemical Constitution of Agar–agar. XIX Pyruvic Acid . . . Agar" *Bull. Chem. Soc. Japan* (1957) 30: 68–70.

R. Isobe et al., "Direct Microznalysis by Negative Ion Fast Atom Bombardment Mass Spectometry" *Trends in Anal. Chem.* (1987) 6: 78–81.

U. Kikkawa et al., "Rapid Purification of Protein Kinase C by High Performance Liquid Chromatography" *Biochem. Biophys. Res. Commun.* (1986) 135: 636–643.

Y. Kishimoto et al., "6–Acyl Galactosyl Ceramides of Pig Brain: Structure and Fatty Acid Composition" *J. Lipid Res.* (1968) 9: 27–33.

E. Klenk & Debuch, "Plasmalogens", *Prog. Chem. Fats Lipids* (1963) 6: 1–29.

N.K. Kochetkov et al., "Table II—The Effects of ATP and Coenzyme A on the Acylation of Lysophospatidylinositol" *Biochim. Biophys. Acta* (1962) 60: 431–432.

N.K. Kochetkov et al., "Sphingoplasmalogens. A New Type of Sphingolipids" *Biochem. Biophys Acta* (1963) 70:716–719.

M. Kubota & T. Taketomi, "Minor Glycolipids Being Less Polar Than Cerebroside in Porcine Spinal Cord" *Jap. J. Exp. Med.* (1974) 44: 145–150.

R.A. Laine et al., "Gas–Liquid Chromatography of Carbohydrates" *Meth. Enzymol.* (1963) 28: 159–167.

G. Larson et al., "Application of a Simple Methylation Procedure for the . . . Glycosphingolipids" *Carbohydrate Research* (1987) 161: 281–290.

A.H. Merrill & V.L. Stevens, "Modulation of Protein Kinase C and Diverse Cell Functions by Sphingosine—a Pharmacologically . . . Transduction" *Biochim. Biophys. Acta* (1989) 1010: 131–139.

T. Miyatake & K. Suzuki, "Globiod Cell Leukodystrophy: Additional . . . Galactosidase" *Biochem. Biophys. Res. Commun.* (1972) 48: 538–543.

S. Neuenhofer et al., "Occurrence of Lysoganglioside . . . Brain" *Biol. Chem. Hoppe–Seyler* (1986) 367: 241–244.

G.A. Nores et al., "Synthesis and Characterization of . . . Compounds" *Carbohydrates Research* (1988) 179: 393–410.

W.T. Norton & M. Brotz, "New Galactolipids of Brain: A Monoalkyl–monoacyl–glycerol . . . Esters" *Biochem. Biophys. Res. Commun.* (1963) 12: 198–203.

Y. Ohashi et al., "Analysis of Long–chain Bases in Sphingolipids by Positive . . . Spectometry" *Biochemistry* (1987) 26: 3390–3395.

M.M. Rapport & R.E. Franzl, "The Structure of Plasmalogens–III. The Nature and Significance of . . . Linkage" *J. Neurochem.* (1957) 1: 303–310.

M.M. Rapport et al., "The Struture of Plasmalogens. II. Crystalline . . . Phospholipide)" *J. Biol. Chem.* (1957) 225: 859–867.

C.C. Sweeley et al., "Gas–Liquid Chromatography of Trimethylsilyl Derivatives . . . Substances" *J. Am. Chem. Soc.* (1963) 85: 2497–2507.

Y. Tamai, "Further Study on the Faster Running Glycolipid in Brain" *Jap. J. Exp. Med.* (1968) 38: 65–73.

Y. Tamai et al., "New Glycolipids in Bovine Brain" *Jap. J. Exp. Med.* (1967) 37: 79–81.

J.B. Wittenberg et al., "The Determination of Higher Fatty Aldehydes in Tissues" *J. Biol. Chem.* (1956) 219: 39–47.

R.K. Yu & R.W. Ledeen, "Gangliosides of Human, Bovine and Rabbit Plasma" *J. Lipid Res.* (1972) 13: 680–686.

R. Feulgen & K. Voit, "Uber Einen weitverbreiteten festen Aldehyde" *Pfluger's Archiv fue die Gesampte Physiologie* (1924) 206: 389–410.

R. Feulgen et al., "Zur Kenntnis des Plasmalogens" *Hoppe–Seyler's Z. Physiol. Chem.* (1929) 180: 161–180.

Feulgen & Grunberg, "Quantitative Bestimmung des Plasmals (Plasmalogens) in Lipoiden Gemischen und in Organen" *Hoppe–Seyler's Z. Physiol. Chem.* (1938) 257: 161–172.

R. Fuelgen & T. Bersin, "Zur Kenntnis des Plasmalogens" *Hoppe–Seyler's Z. Physiol. Chem.* (1939) 260: 217–245.

H. Debuch & M. Winterfeld, "Uber die Struktur der $C_{18}$–und $C_{20}$—Monoenaldehyde aus den Plasmalogenen menschlicher Placenten" *Hoppe–Seyler's Z. Physiol. Chem.* (1970) 351: 179–183.

E. Klenk et al., "Über die Aldehyde der Glycerinphosphatide des Skelett– und Herzmuskels" *Hoppe–Seyler's Z. Physiol. Chem.* (1952) 290: 246–251.

E. Klenk & M. Doss, "Uber das Vorkommen von Estercerebrosiden im Gehirn" *Hoppe–Syler's Z. Physiol. Chem.* (1952) 346: 296–298.

E. Klenk & J.P. Lohr, "Uber die Estercerebroside des Gehirns" *Hoppe–Seyler's Z. Physiol. Chem.* (1967) 348: 1712–1714.

Venberg et al., "Sphingosine and its natural compounds. Ix. Possible selective protection of hydroxyl group on galactocerebrosides" *Chemical Abstracts* (1974) 81: entire abstract.

Manev et al., "Glutamate induced Neuronal Death in Primary Culture of Cerebellar Granule Cells . . . " *The Journal of Pharmacology and Experimental Therapeutics* (Jan. 1990) 252: No. 1.

A. Lehninger, "The Molecular Basis of Cell Structure and Function" *Biochemistry* (1970) pp. 189–192.

Robert L. Lester et al., "The Isolation and Partial Characterization of Two Novel . . . ceramide" *Journ. of Biol. Chem.* (1974) 249: 3388–3394.

Cavaillon et al. *Eur. J. Immunol.* 1986, 16, 1009–1012.

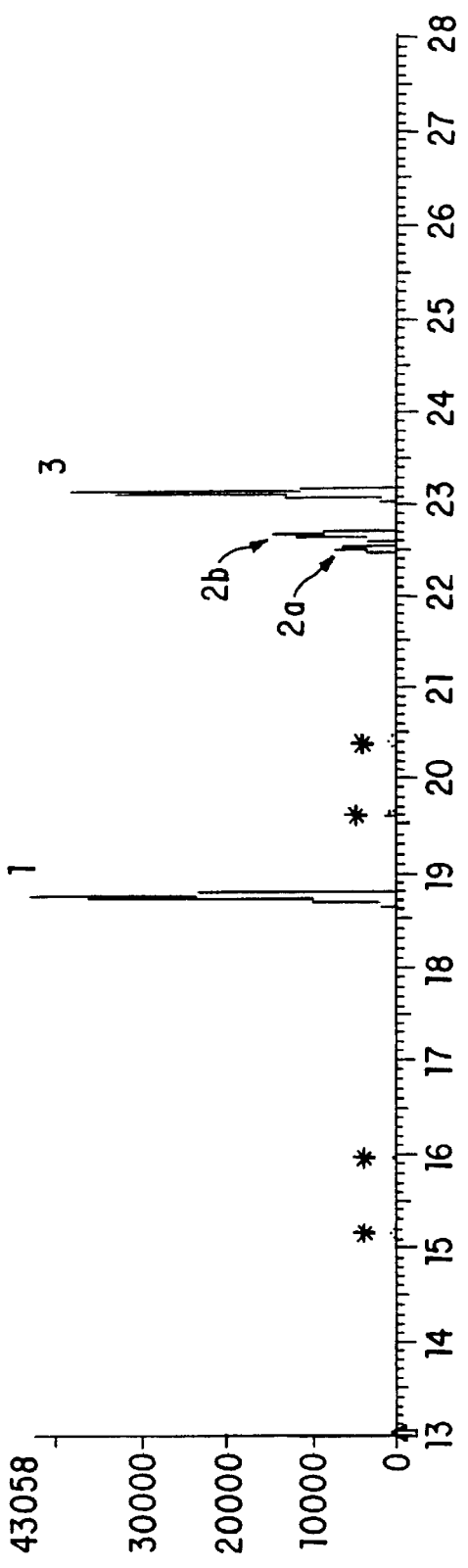
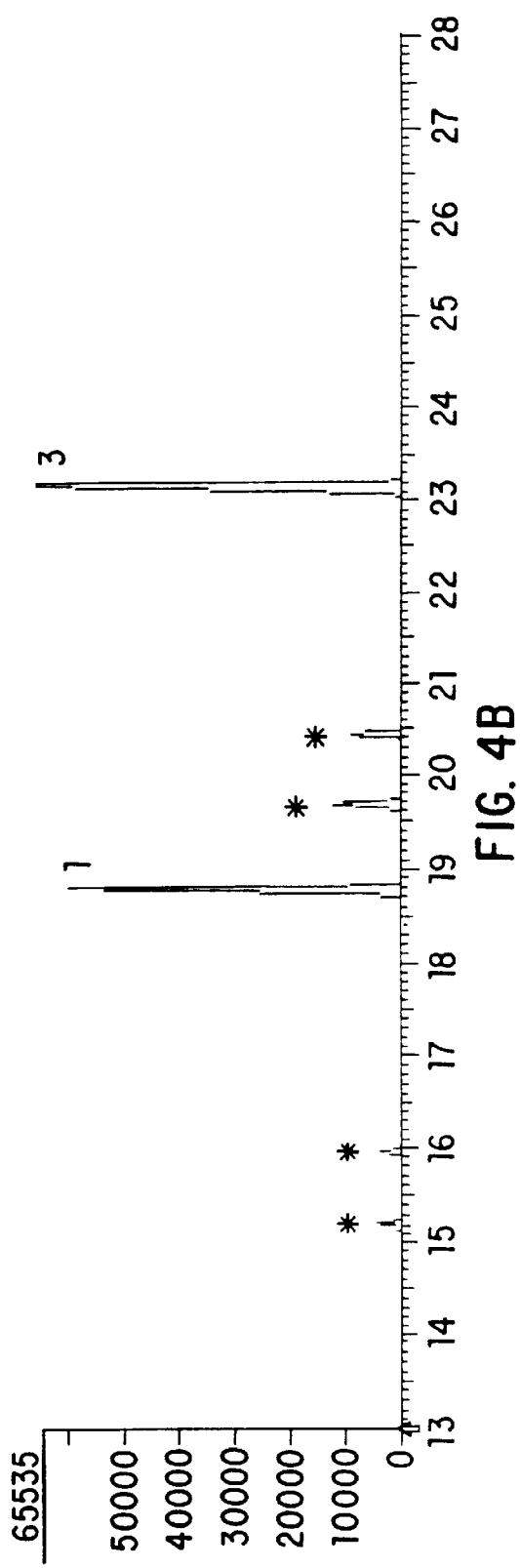
FIG. 4A
FIG. 4B 1 2 3 4 5 6 7 8 9 10 11 12

PLASMALOPSYCHOSINES AND PLASMALOCEREBROSIDES

This is a division of Ser. No. 08/355,276 filed 12 Dec. 1994, now U.S. Pat. No. 5,693,620, which is a continuation-in-part of application Ser. No. 08/079,544 filed 22 Jun. 1993 (abandoned), which is a continuation of Ser. No. 07/738,375 filed 31 Jul. 1991 (abandoned).

FIELD OF THE INVENTION

The instant invention relates to two newly isolated compounds A and B, collectively termed "plasmalopsychosines." Compound A is psychosine with a 3,4 cyclic acetal. Compound B is psychosine (galactosylsphingosine) with a 4,6 cyclic acetal of an aldehyde. Those compounds display remarkable neuritogenic activities in a variety of neural cells, such as, neuroblastoma cells.

The instant invention also relates to two newly isolated compounds C and D, collectively termed "plasmalocerebrosides". Compound C has an aliphatic aldehyde conjugated through a 3,4 cyclic acetal linkage at the galactopyranosyl moiety of a cerebroside. Compound D has an aliphatic aldehyde (plasmal) conjugated through a 4,6 cyclic acetal linkage at the galactopyranosyl moiety of a cerebroside.

In the above, compounds, the fatty aldehyde is derived generally from fatty acids and thus, can have a length dependent on the known fatty acids. Thus, the fatty aldehyde can be, among others, palmital (C16:0), stearal (C18:0) or one having an olefinic double bond (C18:1).

BACKGROUND OF THE INVENTION

Lipid components of cells are generally either acidic or neutral. Acidic lipids include gangliosides, sulfatide, phosphoinositide and phosphatidic acid. Neutral lipids include neutral glycolipids and neutral glycerides. Anionic (basic) lipids such as sphingosine, N,N-dimethyl-sphingosine and lyso-glycosphingolipids are assumed to be present as minor components modulating cellular functions, such as transmembrane signaling (1–4).

Kotchetkov et al. (13) described "sphingoplasmalogen" as a minor component of chromatographically fast-migrating cerebroside in brain. The compound was assumed to have a structure with fatty aldehyde linked to the C3 hydroxyl group of galactosyl cerebroside through an unsaturated ether bond, based on infrared spectroscopy (absence of absorption at 1750 $cm^{-1}$ for ester linkage); fatty aldehydes were identified as p-nitro-phenylhydrazide under Wittenberg's conditions (14). The structure was claimed to be as shown below and termed "sphingo-plasmalogen".

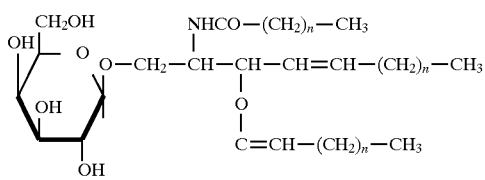

However, the presence of sphingoplasmalogen or any bound aliphatic (fatty) aldehyde (plasmal) in glycosphingolipid was denied in four subsequent investigations (18, 42, 43, 44). Further, extensive studies of multiple fast migrating cerebroside extensively studied by Klenk and Löhr (15), Tamai et al. (16,17) and Kishimoto et al. (18) concluded that all those fast-migrating glycosphingolipids are cerebrosides esterified at different positions of the hydroxyl groups with fatty acid. The previously-reported compounds, whether sphingoplasmalogen or fast-migrating ester cerebrosides, showed very different thin-layer chromatography mobility compared to the plasmalopsychosines of the instant invention. That is, the plasmalopsychosines of the instant invention have much slower mobility and have two aliphatic chains (one sphingosine, one plasmal); also, the orientation of the aliphatic chains linked to the galactopyranosyl moiety appears to be in an entirely opposite direction.

The fatty aldehyde (or long-chain aliphatic aldehyde), termed "plasmal," was originally discovered by Feulgen & Voit in 1924 (19), and was recognized as a component of a glycerophospholipid termed plasmalogens in 1929 (6). The structure of plasmalogen, originally claimed to be a 1,2-cyclic acetal linkage (37), was eventually identified as 1-alkenyl-2-acyl-3-phosphorylcholine (20).

A class of cerebrosides containing a fatty acid ester group and termed ester cerebrosides have been isolated from brain. The compounds were shown to have much higher thin-layer chromatography (TLC) mobility than regular cerebroside (39,40). The locations of the fatty acid were identified to be the C3 hydroxyl group of sphingosine and the C3 or C6 hydroxyl group of galactose (15, 16, 17, 18).

Neuroblastoma cell lines have been widely used to screen substances having possible promoting effects on neuritogenesis in vivo. Some gangliosides and synthetic sialosyl compounds are potent stimulators of neuritogenesis, particularly in the presence of nerve growth factor. In a recent study, administration of a ganglioside/nerve growth factor (NGF) mixture to patients with Alzheimer's syndrome was claimed to improve clinical symptoms (21). Similarly, following neural tissue damage provoked by various factors, administration of a ganglioside mixture has been claimed to produce partial recovery.

In view of the possible involvement of sphingosine, N,N-dimethylsphingosine and lysoglycosphingolipids in modulation of transmembrane signaling (1–4) chemical identification, purification and characterization of those compounds occurring naturally in neural tissue is of great interest.

SUMMARY OF THE INVENTION

Accordingly, one object of the invention is to provide four isolated or synthetic compounds that show remarkable neuritogenic activity.

Another object of the invention is to provide compositions and methods for inducing neuronal development.

Those and other objects have been achieved by providing an isolated or synthetic plasmalopsychosine selected from the group consisting of compound A and compound B:

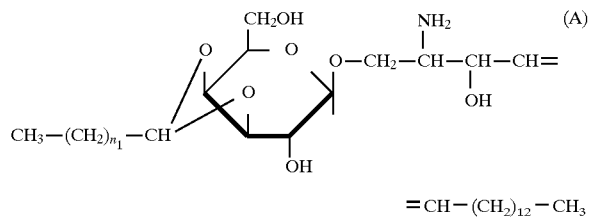

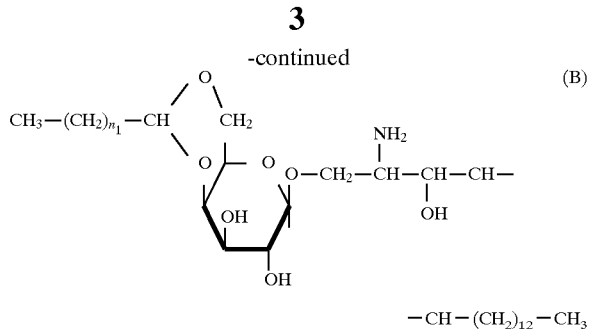

(B)

wherein n1 and $n_1$ each is 0 to about 50, and biologically compatible salts thereof.

The objects of the instant invention also have been achieved by providing an isolated plasmalocerebroside selected from the group consisting of compound C and compound D:

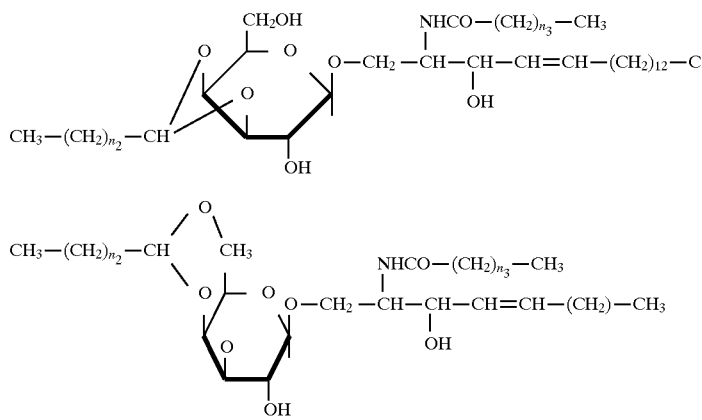

wherein n2, n3, $n_2$ and $n_3$ each is 0 to about 50, and biologically compatible salts thereof.

The instant invention also provides a composition for inducing neuronal development comprising one or more of the above-described plasmalopsychosines and/or plasmalocerebrosides and biologically compatible salts thereof; and a biologically acceptable carrier, diluent or excipient.

The instant invention further provides a method forming neurites from nerve cells comprising contacting the cells with an effective amount of one or more of the above-identified plasmalopsychosines and/or plasmalocerebrosides.

The instant invention additionally provides a method of treating neuronal diseases and tissue damage comprising administering to a host in need of treatment a biologically effective amount of one or more of the above-described plasmalopsychosines and/or plasmalocerebrosides.

BRIEF DESCRIPTION OF THE FIGURES

FIG. 1A: thin-layer chromatograph was developed in chloroform-methanol-28% $NH_4OH$ (80:20:2). Bands were detected by orcinol-sulfuric acid. Lane 1, total eluate from carboxymethyl SEPHADEX column with 0.5M triethylamine; lane 2, purified compound A; lane 3, purified compound B; lane 4, purified compound E; lane 5, sphingosine. FIG. 1B: The same chromatogram as in FIG. 1A. Bands were detected by spraying with 0.01% PRIMULINE and viewed under UV light.

FIGS. 4A and 4B are the data from gas chromatography-chemical ionization/mass spectrometry (GC-Cl/MS) of long chain methyl enol ethers: FIG. 4A, from methanolysis of the middle band lipid; FIG. 4B, from methanolysis of standard n-16:0 and n-18:0 aldehydes. Peaks were identified as 1, 16:0; 2a and 2b, isomeric 18:1; and 3, 18:0 methyl enol ethers, having pseudomolecular ion masses of 255, 281, and 283 u, respectively. Peaks marked by asterisk are impurities common to both samples, probably arising from the derivatization reagents.

FIG. 5A, $^+$FAB mass spectrum of upper band lipid in 3-nitrobenzyl alcohol (NBA) matrix; FIG. 5B, $^+$FAB mass spectrum of middle band lipid in NBA matrix; FIG. 5C, $^+$FAB mass spectrum of middle band lipid in NBA/sodium acetate matrix; and FIG. 5D, FAB mass spectrum of middle band lipid in triethylamine (TEA) 15-crown-5 matrix.

FIG. 6A, upper band lipid, following brief acid treatment, resulting in conversion to middle band lipid; FIG. 6B, upper band lipid following extended acid treatment; FIG. 6C, lower band lipid following extended acid treatment; and FIG. 6D, d 18:1 galactopsychosine standard.

FIG. 7A, peracetylated upper band lipid in NBA matrix; FIG. 7B, peracetylated middle band lipid in NBA matrix; FIG. 7C, peracetylated middle band lipid in NBA/sodium acetate matrix; and FIG. 7D, peracetylated and de-O-acetylated middle band lipid in NBA matrix (inset: same product in NBA/sodium acetate matrix, showing no change in masses of pseudomolecular ions).

FIG. 8A, PMAA from upper band lipid; FIG. 8B, PMAA from middle band lipid; FIG. 8C, PMAA from upper band lipid following brief acid treatment; and FIG. 8D, standard galactose PMAA's. Peaks are identified as PMAAs of 1: 2,3,6-tri-O; 2: 3,4,6+2,4,6-tri-O; 3: 2,3,4-tri-O; 4: 2,6-di-O; 5: 4,6-di-O; 6: 3,6-di-O; 7: 2,3-di-O, 8: 6-mono-O-; 9: 3,4-di-O; 10: 2-mono-O-; and 11: 3 (or 4)-mono-O-Me-Gal.

FIGS. 9A and 9B show different areas of the culture dish.

FIG. 18A: data from fraction of FIG. 17 Lane 5 product; FIG. 18B: data from fraction of FIG. 17 Lane 4 product; Figure C: standard PMAA's.

DETAILED DESCRIPTION OF THE INVENTION

Figure 1A:
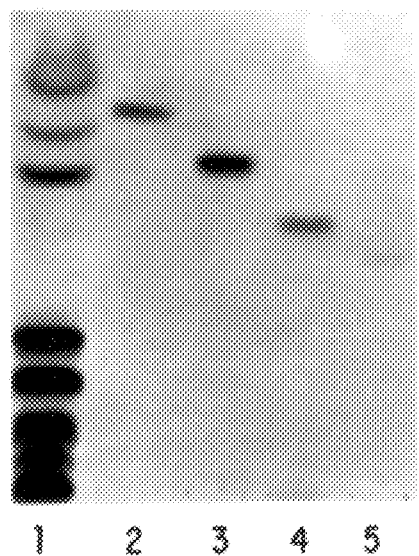
FIGS. 1A and 1B are high-performance thin-layer chromatography (HPTLC) patterns of anionic lipids adsorbed on carboxymethyl SEPHADEX and eluted with triethylamine in chloroform-methanol mixture.

The instant compounds comprise hydrocarbon chains of varying length. Because the hydrocarbon chains in vivo are derived generally from fatty acids, the size of the hydrocarbon side chains of the instant compounds are definable in terms of the sizes of the fatty acids. Common fatty acids include palmitic acid ($C_{16}$), stearic acid ($C_{18}$), oleic acid ($C_{18}$, one unsaturated bond) and linoleic acid ($C_{18}$, two unsaturated bonds). Fatty acids generally have an even number of carbon atoms. The fatty acids can be saturated or not.

But in the instant compounds (A) and (B), as well as in (C) and (D), the side chains can have any of a variety of lengths determinable, in part, by the size of fatty acids but also, can be of other sizes based on the desired size of the side chain reagents used in the synthetic schemes disclosed hereinbelow. Thus, in compounds (A) and (B), $n_1$ can be 0 or any number up to about 50. Based on the known fatty acids, $n_1$ can be from about 14 to up to about 24 as the largest fatty acid known to date is a $C_{26}$ fatty acid. In view thereof, the size of the side chains can vary considerably with the proviso that the resultant compound is biologically compatible. Preferred compounds are those which have side chains which correspond to the sizes of known fatty acids.

The instant plasmalopsychosines (A) and (B) are notable by the free amino group on the sphingosine portion of the molecule. Moreover, the instant compounds comprise a plurality of charged groups which may be amenable to salt formation on reaction with suitable cations and anions. The salts do not alter the biologic activity of the instant compounds as is described, that is, for example, enhances neuronal or neurite growth, but may enhance some of the physical characteristics of the instant compounds, for example, enhance solubility in aqueous media. Pharmaceutically acceptable salts are those instant compounds carrying complexed cations and/or anions without detracting from the biological activity thereof and which are suitable for in vivo use.

ISOLATION AND PURIFICATION OF PLASMALOPSYCHOSINE COMPOUNDS A AND B

A procedure for systematic isolation and characterization of anionic lipid through cation exchange chromatography in chloroform-methanol followed by a series of chromatographies on a FLORISIL and IATROBEADS column has been developed. The major anionic lipids, compounds A and B, present exclusively in the extract of white matter, have been identified as cyclic plasmal linked at different hydroxyl groups of the galactosyl residue of psychosine. Isolation, chemical characterization, and biological properties of these compounds are hereby described.

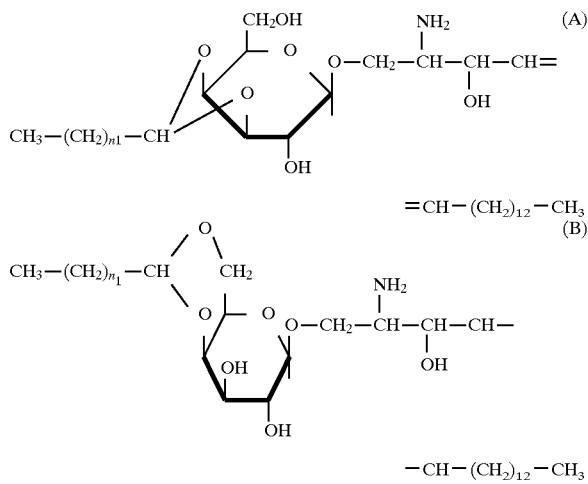

n1 and $n_1$ each is 0 to about 50 and preferably 14–24.

According to the instant invention, white and gray matter of human brain were carefully separated and subjected to systematic chemical analysis. As a result, two major anionic glycolipids, termed compounds A and B, were identified as plasmal (fatty aldehyde) conjugated with psychosine through 3,4-cyclic acetal and 6,4-cyclic acetal linkage, respectively, at the galactosyl residue of psychosine. A relatively minor compound E was identified as 4,6-cyclic plasmal conjugate of psychosine but had 3-hydroxysphingosine. Those three compounds are hereby collectively termed "plasmalopsychosines." Plasmalopsychosines, regardless of the position of the acetal linkage, have strong neuritogenic effects on neuroblastoma cells, particularly in the presence of nerve growth factor (NGF).

More specifically, compounds A and B can be isolated by preparing anionic lipids and anionic glycosphingolipids from human brain. The lipids are extracted and a lower layer is prepared. That is followed by separation of the anionic lipid fraction by carboxymethyl (CM) SEPHADEX chromatography. The isolated compounds A and B can be further purified by high-performance thin-layer chromatography (HPTLC), followed by high-performance liquid chromatography (HPLC) (IATROBEADS).

The isolation and purification procedure is described in more detail below and exemplified in Example 1.

Preparation of anionic lipids and anionic glycosphingolipids

Extraction and preparation of lower layer. Human brain (cerebrum) is dissected and separated into gray and white matter with a razor blade. With careful practice, using a razor blade to scrape the outer layer of cortex, it is possible to obtain a near-pure gray matter fraction weighing about 50 g from adult human brain. White matter is considerably easier to prepare by cutting the brain into vertical sections and separating large areas of white matter. In both cases, tissue is homogenized in about five volumes (i.e., five times volume/weight of wet tissue) of isopropanol/hexane/water (IHW) (55:25:20 v/v/v, upper phase removed: when this solvent solution is prepared, two phases form and the upper phase which is predominantly hexane is removed), filtered over a Büchner funnel and the residue is re-homogenized in the same solvent. (Hereinafter, all references to ratios of solvents are by volume.) After the first filtration over the Büchner funnel, the residue is rehomogenized twice in chloroform/methanol/water (CMW) (2:1:0.1). The filtrates are pooled, evaporated to dryness, and brought up in chloroform/methanol (2:1) to a suitable volume (for example, about 0.5–3 L for 500 gm starting tissue) for Folch's partition (5). For Folch partition, one-sixth volume deionized water is added to the chloroform/methanol (2:1) extract solution in a leak-proof container and the contents are mixed by repeated inversions (about 20). After the phases resolve (usually 2 to 3 hours), the upper phase is drawn off and replaced with an equal volume of chloroform/methanol/water with 0.2% KCl (1:10:10). That is repeated two additional times and the resulting lower phase is evaporated to dryness by rotary evaporator.

Separation of anionic lipid fraction by carboxymethyl (CM) SEPHADEX chromatography. The anionic lipid fraction is prepared from the total lower layer lipid by CM SEPHADEX chromatography. CM SEPHADEX is washed and equilibrated using the following protocol. It is crucial that the SEPHADEX is equilibrated properly to achieve effective binding of anionic lipids. The dry resin is washed extensively over a Büchner funnel in 0.2N HCl and allowed to soak for several hours in the acid. The resin is then washed extensively with deionized water with intermittent soaking, followed by stepwise washing of methanol/water (MW) 20:80, 50:50, 70:30 and 90:10. Subsequently, the SEPHADEX column is soaked in a solution of 2.0M aqueous triethylamine (TEA)-MW (1:1:1) and allowed to sit at room temperature overnight. Excess TEA is removed from the SEPHADEX by extensive washing in MW 1:1. The equilibrated CM SEPHADEX then is washed with 100% methanol followed by CMW 40:60:5 (hereinafter "sol A").

To the dried lower phase of brain extract, sol A is added until the brain extract is dissolved. For 500 gm of tissue, about 1 L solvent is required. That solution is passed over a bed of equilibrated CM SEPHADEX having a volume of 50–200 ml (about 100 ml per kg wet tissue) and allowed to elute by gravity filtration. An additional amount of sol A is washed through the column and the total pass-through fraction is collected and saved. The column then is washed with MW 90:10 until the bed volume is equilibrated (the SEPHADEX will shrink slightly). Anionic lipids are eluted using a solution of 0.5M TEA in MW 90:10 (titrated to a pH of 9.25 by gently bubbling $CO_2$ gas through the solvent). For 500 gm starting tissue, about 500 ml of about 0.5M TEA is sufficient to quantitatively elute compounds A and B, as well as compound E and sphingosine. That concentration of TEA also quantitatively elutes standard psychosine, although psychosine is absent in brain extract. Further, increasing the TEA concentration up to 2.0M does not result in elution of any other detectable species.

Further purification of compounds A, B and E using HPLC IATROBEAD chromatography The 0.5M TEA fraction from CM SEPHADEX is evaporated to dryness several times using absolute ethanol to rid the sample of TEA. The fraction then is transferred to a test tube and dissolved in a suitable volume of chloroform/methanol (about 2–10 ml). Ten µl of the sample is chromatographed on high-performance thin-layer chromatography (HPTLC) plates in chloroform/methanol-$NH_4OH$ 80:20:2. Viewing can be accomplished with a hand-held UV light using either 0.8% PRIMULIN in 80% acetone or 30% FLUORESCAMINE. It also is possible to detect compounds A, B and E with 0.5% orcinol in 10% sulfuric acid followed by baking in a thin layer chromatography (TLC) oven.

To separate compounds A, B and E from the more polar sphingosines and contaminating neutral glycolipids, it is necessary to perform several high performance liquid chromatography (HPLC) gradient runs. That is accomplished using a very nonpolar IHW gradient. A long column (e.g., about 0.4×60 cm) packed with IATROBEADS (silica gel; 10 $\mu$M) is first equilibrated by washing the column as follows: at about 2.0 ml/min the starting concentrations are IHW 55:40:5; the gradient is increased to IHW 55:25:20 over about the next 30 minutes, followed by decreases to IHW 55:40:5 for about 30 minutes, IH 60:40 for about 30 minutes and finally washing with hexane 100% for about 30 minutes.

The 0.5M TEA fraction is prepared for injection by evaporating to dryness and dissolving in 100% hexane in the following manner. For a 2 ml injection, 100 $\mu$l of chloroform/methanol (2:1) is added, the cap is screwed on tightly and the sample is warmed to about 50° C. and sonicated to form a thick oil. In most cases, that almost completely solubilizes the lipid. To that thick oil, 2 ml of 100% hexane is added while sonicating. In some cases, a very fine, opalescent precipitate forms, but that does not interfere with the injection.

The sample is loaded onto the column and subjected to a gradient eluting at about 0.5 ml/min. Gradient elution is started from the hexane to IHW 10:89:1 (about 25 to 150 minutes) and continues to IHW 24:74:2 (about 150 to 400 minutes), to IHW 55:40:5 (about 400 to 500 minutes) and to IHW 55:25:20 (about 500 to 600 minutes). Effluent (about 3 ml/tube) is collected over a fraction collector in 100 tubes and the tubes are streaked for HPTLC analysis (chloroform/methanol/NH$_4$OH, 80:20:2). Fractions are pooled based on separation of three detectable bands corresponding to compounds A, B and E. However, due to sphingosine overlap, several HPTLC runs are necessary to purify the compounds A, B and E to homogeneity. In that manner, sphingosine also is purified, as well as a slower migrating sphingosine analog. Chemical characterization of plasmalopsychosine compounds A and B Carbohydrate analysis can be performed by gas chromatography-mass spectrometry (GC-MS) employing trimethysilyl derivatives of methyl glycosides produced by methanolysis. Fast atom bombardment-mass spectrometry (FAB-MS) analysis of native lipid can be obtained in both positive and negative ion modes (7–9). Preliminary analysis of fatty aldehydes can be made using fatty acid methyl ester fraction yielded on methanolysis of lipids. However, a number of unknown peaks will be identified as enol methyl ether of C16–C18 fatty aldehyde, in addition to fatty acid methyl esters. The peaks are identified using GC-MS in conjunction with FAB-MS analysis. Structural information also can be obtained by FAB-MS of per-N-O-acetylated and de-O-acetylated lipids and by classical methylation analysis with GC-MS.

ISOLATION AND PURIFICATION OF CEREBROSIDE COMPOUNDS C AND D

In the instant study, during investigation of fast-migrating (on thin-layer chromatography) glycolipids from human brain, an acid-labeled minor component was detected and separated by successive chromatographies on columns of FLORISIL and IATROBEADS (silica gel) in an isopropanol/hexane/water system and preparative high-performance thin-layer chromatography. In contrast to the majority of fast-migrating glycolipids, which were identified as fatty acid esters of cerebroside, the acid-labile minor component was isolated and characterized as a plasmal conjugate of cerebroside, through 3,4-cyclic or 4,6-cyclic acetal linkage at the galactopyranosyl residue of cerebroside.

Isolation, chemical characterization and biological activity of those compounds are described hereinbelow.

Isolation of plasmalocerebrosides

According to the instant invention, the two newly isolated plasmalocerebrosides which are designated compound C and compound D have the structures shown below:

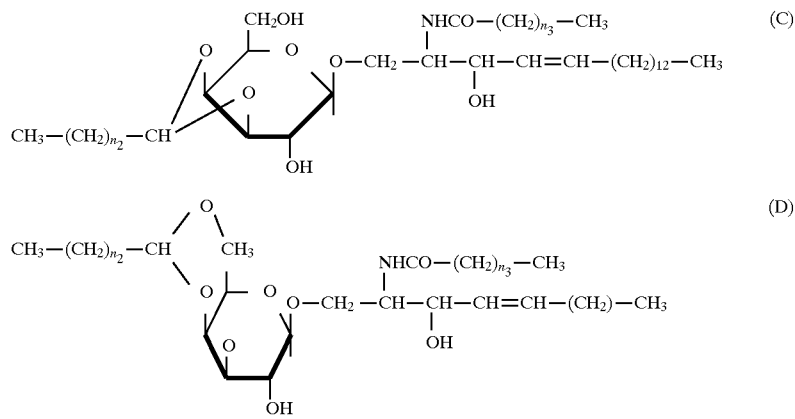

wherein n2, n3, n$_2$ and n$_3$ each is 0 to about 50, and pharmaceutically acceptable salts thereof. Preferably n2 or n$_2$ is 14–24 and n3 or n$_3$ is 14–24.

Instant compounds (C) and (D) also contain hydrocarbon chains derived in vivo from fatty acids. Hence, it is not uncommon for the sidechains containing n$_2$ and n$_3$ to have a size determinable by the size of known fatty acids. Thus, preferred sizes of the side chains in terms of the size of the n groups are from about 14 to about 24, which correspond to the known fatty acids with a C$_{26}$ being the largest known fatty acid. But the side chains can be larger or smaller when the compounds (C) and (D) are synthesized using the methods disclosed herein and using reagents for making the side chaims of different lengths. Hence, the side chains can be up to about 50 in size with the proviso being that the resulting compound being biologically compatible and retaining the activities disclosed herein.

To isolate compounds C and D, a fast-migrating component from column chromatography of a human brain cerebroside extract is isolated first. The human brain cerebroside fraction can be obtained by homogenization of brain tissue with about five volumes (i.e., five times volume/weight of wet tissue) of isopropanol/hexane/water (IHW) 55:25:20 (v/v/v) and filtration through a Büchner funnel. The residue is rehomogenized in the same volume of the same solvent. The extracts are pooled, evaporated to dryness and subjected to Folch partition using about 1 L of chloroform/methanol (CMe) 2:1 and about 166 ml water per 10 g original wet weight of tissue. The lower phase is subjected to Folch partitioning three more times and then repartitioned with "theoretical upper phase" (chloroform/methanol/water with 0.2% KCl 10:10:1). The resulting lower phase is evaporated to complete dryness. A large column (bed volume about 1 L per 1 kg original tissue) of FLORISIL (a mixture of magnesium oxide and silicic acid gel) (from Sigma; mesh 60–100) is prepared and equilibrated in pure hexane. The dried lower phase is suspended in hexane (about 1 L per 200 g original tissue), passed over the FLORISIL column and exhaustively washed with about 4 L of hexane. The FLORISIL column is then eluted with 2 L of hexane/dichloroethane (DCE) 2:1, then with 2 L of DCE and finally with 1 L of DCE/acetone 1:1. The final eluate contains the desired acid-labile fast-migrating component.

The presence of acid-labile glycolipids can be detected by hydrolysis of samples in methanol/aqueous 0.1N HCl (1:1, v/v) heated at about 90° C. for about 10 minutes, followed by Folch partitioning and thin-layer chromatography (TLC) examination of the lower phase. The glycolipid with high TLC mobility which is converted to the same mobility as cerebrosides by this treatment is regarded as the acid-labile cerebroside. Cerebroside and ester cerebroside do not show altered TLC mobility under these conditions.

Isolation and preliminary characterization of acid-labile glycosphingolipids present in the fast-migrating fraction According to the instant invention, the presence of an acid-labile fast-migrating glycolipid is a consistent component of brain extract, and is found in the unabsorbed fraction on carboxymethyl-SEPHADEX and diethylaminoethyl-SEPHADEX of the Folch's lower phase as well as in the DCE-acetone 1:1 eluate fraction on chromatography over FLORISIL. The fast-migrating glycolipid fraction is further purified by high-performance liquid chromatography (HPLC) on an IATROBEADS column loaded in pure hexane and eluted with a gradient to IHW 55:50:5 at about 1 ml/min for about 3 hours. Fractions are collected into 200 tubes. The acid-labile glycolipid component is eluted in tube Nos. 130–154. The pooled fraction (called fraction VI) contains most of the acid-labile glycolipid and is free of cerebroside and ester cerebrosides. The fraction VI further is purified by chromatography on IATROBEADS, loading on the columns in pure hexane and subjected to a gradient up to isoproponal/hexane (IH) 30:70. The fraction VI A thus obtained is purified further on a long IATROBEADS column (e.g., about 0.5×100 cm) with a shallow gradient, loaded with pure hexane and gradient eluted to IHW 50:40:5 for 3 hours. Alternatively, the compounds can be purified by preparative TLC. A homogeneous band is obtained as shown in FIG. 1 1, lane 6. On TLC, the compounds migrate faster than cholesterol which migrates faster than ester cerebrosides. The compounds do not contain sulfate or sialic acid which are known to be acid-labile.

Chemical characterization of compounds C and D

The structure of compounds C and D can be determined after methanolysis by identifying enol methyl ethers derived from fatty aldehydes by gas chromatography-mass spectrometry (GC-MS) analysis and by fast atom bombardment mass spectrometry (FAB-MS) as described in detail in the Example 7.

The acetal linkage can be determined by methylation analysis. Following permethylation, acid hydrolysis, reduction, and acetylation of the native lipid, the resulting partially methylated hexitol acetates are analyzed by GC-MS as described in detail in Example 7.

METHOD OF FORMING NEURITES FROM NERVE CELLS

According to a further aspect of the instant invention, neurites can be formed from nerve cells by contacting the nerve cells with an effective amount of one or more of the compounds A, B, C and D. The nerve cells, such as from neuroblastoma cell lines, are cultured in gelatin-coated plates by known methods (11,12). The effective dose is determined by adding various concentrations (e.g., 5–150 $\mu$M) of one or more of compounds A, B, C and D, and the cells are cultured for the observation of neurite formation, as described in more detail in Example 8. The instant invention can find use in the treatment and maintenance of organ, tissue and cell explants awaiting transplantation. Thus, the instant invention encompasses compsitions comprising one or more of compounds (A), (B), (C) or (D) and a biologically compatible carrier or diluent.

COMPOSITION AND METHOD FOR TREATING NEURONAL DISEASES AND TISSUE DAMAGE

Both psychosine compounds A and B display remarkable neurogenic activity in a variety of neuroblastoma cells. Neurite formation in neuroblastoma and retinoblastoma cells often is used as a criterion to evaluate ability of candidate reagents to repair neuronal tissue damage.

The effect of compounds A and B on neurite formation in neuroblastoma cells, in comparison to existing gangliosides, is presented in detail in Example 8. Thus, whereas psychosine is highly hemolytic and assumed to be highly cytotoxic, it is virtually absent in normal brain tissue (either white or gray matter). In contrast, plasmalopsychosine, a major component of white matter, shows strong neuritogenic activity in neuroblastoma cells. Psychosine used as a control in these experiments showed cytotoxic effects and inhibited cell growth even at very low doses. Plasmalopsychosine does not inhibit PKC, in contrast to the strong inhibitory effect of psychosine. While not wanting to be bound by the following hypothesis, it is possible that plasmalopsychosine is incorporated into cells and is converted to psychosine and thereby regulates activity of PKC and other protein kinases essential for cell growth regulation. Growth inhibition subsequently induces differentiation. The quantity of psychosine generated could be minimal but yet optimal for stimulation of differentiation and neurite formation.

Both plasmalocerebroside compounds C and D also display remarkable neurogenic activity in a variety of neuroblastoma cells. No clear effect in the early stages of cell culture is observed, but neurite formation, i.e. neurites >50 $\mu$m long, becomes increasingly apparent by 1 week. After 2 weeks of culture, neurite formation in Neuro-2A cell culture is very pronounced.

Accordingly, the instant invention provides a composition for treating neuronal diseases and tissue damage comprising one or more of compounds A, B, C and D and pharmaceutically acceptable salts thereof; and a pharmaceutically acceptable carrier, diluent or excipient. The means and method for preparing pharmaceutic preparations is well-known in the art and the artisan can refer to any of a variety of pharmacology text books regarding those non-critical aspects of the instant invention.

The instant invention also provides a method for treating neuronal diseases and tissue damage comprising administering to a host in need of treatment a biologically effective amount of one or more of the compounds A, B, C and D, and pharmaceutically acceptable salts thereof.

Specific cases include treatment of Alzheimer's disease, spinal injury such as paralysis, cerebral vascular accidents where there is loss of neural tissue, brain trauma, Parkinson's disease, amyotropic lateral sclerosis and multiple sclerosis.

The effective amount of compounds A, B, C, and D can be determined using art-recognized methods, such as by establishing dose-response curves in suitable animal models or in non-human primates, and extrapolating to human; extrapolating from suitable in vitro data, for example as described herein; or by determining effectiveness in clinical trials.

Suitable doses of medicaments of the instant invention depend upon the particular medical application, such as the severity of the disease, the weight of the individual, the age of the individual, half-life in circulation, etc., and can be determined readily by the skilled artisan. The number of doses, daily dosage and course of treatment may vary from individual to individual.

For example, the effective doses can be derived from in vitro studies, as described hereinbelow. In the case of neuritogenesis, a concentration of 5–150 $\mu$M was used. Neuritogenesis was obtained, for example, at a concentration of 50 $\mu$M. As is known in the pharmaceutic arts, the kinetics of achieving an appropriate and effective blood concentration depend, for example, on the route of administration, serum molecules which sequester the instant compounds, enzymes that might inactivate the instant compounds and the like. But the pharmacokinetics of the instant compounds can be determined following art-recognized methods, such as, administering radiolabelled compound to a test subject and following the time course of plasma presence, tissue distribution and the like.

Hence, the dose of the instant compounds could be on the order of 5–150 $\mu$M if administered intravenously with the number of doses determinable by the kinetics data and would be adjusted to higher concentrations for an oral or topical form.

Gangliosides also demonstrate a neuritogenic effect but the concentrations of gangliosides required to achieve the same degree of neuritogenesis are on the order of 2–4 times that of an instant compound. Because some gangliosides are used as drugs, see, for example, Samson, "Drugs of Today", volume 22, No. 2, 1986, which teaches CRONASSIAL®, the dosing of gangliosides can be used as a guide for obtaining suitable doses of the instant compounds, that is, 25%–50% that of the dose of, for example, CRONASSIAL.

The most suitable form of administration is oral, but generally higher concentrations are required as are modifications which would render the instant compounds acid resistant. Alternatively, the instant compounds can be contained within microcapsules, such as liposomes, for enhanced delivery. Parenteral forms are prepared using suitable buffers, such as physiologic salines, with accompanying preservatives and the like. Because the distant compounds are hydrophobic molecules, the instant compounds likely would traverse cell membranes with little difficulty and hence would traverse the blood-brain barrier for treating central nervous system targets. Various other methods for traversing the blood-brain barrier can be used, for example, osmotic shock, antibody carriers, liposomes and the like.

A key cellular manifestation of the instant compounds is enhancing neuronal cell growth. That phenomenon is manifest, for example, by enhancing neurite growth. The overt, organismal manifestation of such a cellular action can be many-fold and of a variety of forms. However, a suitable amount of an instant compound is that amount which results in an amelioration of adverse neurologic symptomology. Thus, is tremor is the malady, a biologically effective amount is that lowest or optimized dose based on dose-response studies which would reduce the amount of tremor.

Hence, the biologically effective amount is that amount which yields an observable beneficial change from an abnormal state. The change can be stoppage of disease progression. The determination of a suitable dose thus depends on the abnormal state and is determinable by an artisan practicing known methods, generally an empirical assessment built on cumulative animal and clinical studies. Determination of dose is not a critical aspect of the instant invention.

Because of the relatedness of instant compounds (A), (B), (C) and (D), a plurality of species can be used in place of one species. The amounts of each species initially is that amount which additively would yield the amounts disclosed herein. However, lower doses of some or all of the species in a combination may be used if synergism is present.

The compounds A, B, C and/or D can be administered in a variety of ways such as intravenously or by direct subdural injections. Suitable pharmaceutically acceptable carriers, diluents, or excipients for the medicament of the instant invention depend upon the particular medical use of the medicament and can be determined readily by the skilled artisan.

The medicament can be formulated into solutions, emulsions, or suspensions. The medicament is likely to contain any of a variety of art-recognized excipients, diluents, fillers, etc. Such subsidiary ingredients include disintegrants, binders (including liposomes), surfactants, emulsifiers, buffers, solubilizers and preservatives. The artisan can configure the appropriate formulation comprising compounds A, B, C and/or D by seeking guidance from numerous authorities and references such as "Goodman & Gilman's The Pharmaceutical Basis of Therapeutics" (6th ed., Goodman et al., eds., MacMillan Publ. Co., N.Y., 1980).

CHEMICAL SYNTHESIS OF COMPOUNDS A, B, C, AND D

Plasmalopsychosine compounds A and B and plasmalocerebrosides compounds C and D can be synthesized chemically by a method such as that described for the synthesis of plasmalopsychosine compounds in Example 9.

EXAMPLES

The invention will now be described by reference to specific examples which are not intended to be limiting.

EXAMPLE 1

ISOLATION AND PURIFICATION OF COMPOUNDS A AND B

Preparation of Anionic Lipids and Anionic Glycosphingolipids

Extraction and preparation of lower layer. Adult human brain (cerebrum) was dissected and separated into gray and white matter with a razor blade. With careful practice, using a razor blade to scrape the outer layer of cortex, it was possible to obtain a near-pure gray matter fraction weighing 50 g. White matter was considerably easier to prepare, by cutting the brain into vertical sections and separating large areas of white matter. An entire small brain (cerebellum) was also used as a source of extraction. In all cases, tissue was homogenized in five volumes (i.e., five times volume/weight of wet tissue) of isopropanol/hexane/water (IHW) (55:25:20 v/v/v, upper phase removed), filtered over a Büchner funnel and the residue was rehomogenized in the same solvent. (Hereinafter, all references to ratios of solvents are by volume unless otherwise indicated.) After the first filtration over the Büchner funnel, the residue was rehomogenized twice in chloroform/methanol/water (CMW) (2:1:0.1). All filtrates were pooled, evaporated to dryness and resuspended in chloroform/methanol (2:1) to a suitable volume (0.5–3 L) for Folch's partition (5). For Folch partition, one-sixth volume deionized water was added to a chloroform/methanol (2:1) extract solution in a screw-cap container and the contents were inverted 20 times. After the phases had resolved (usually 2 to 3 hours), the upper phase was drawn off and replaced with an equal volume of "theoretical upper phase" (CMW-0.2% KCl, 1:10:10). That was repeated two additional times, and the resulting lower phase was evaporated to dryness in a rotary evaporator.

Separation of anionic lipid fraction by CM SEPHADEX chromatography. The anionic lipid fraction was prepared from the total lower layer lipid by carboxymethyl (CM) SEPHADEX chromatography. CM SEPHADEX (Sigma, C-25) was washed and equilibrated using the following protocol. It was crucial that the SEPHADEX was equilibrated properly to achieve effective binding of anionic lipids. The dry resin was washed extensively over a Büchner funnel in 0.2N HCl and allowed to soak for several hours in the acid. The resin is washed extensively with deionized water with intermittent soaking, followed by stepwise washing with methanol/water (MW) (20:80, 50:50, 70:30, and 90:10). Subsequently, the SEPHADEX column was soaked in a solution of 2.0M aqueous triethylamine (TEA) (Mallinckrodt)-MW (1:1:1) and allowed to sit at room temperature overnight. Excess TEA was removed from the SEPHADEX by extensive washing in MW (1:1). The equilibrated CM SEPHADEX was then washed with 100% methanol followed by CMW (40:60:5) (hereinafter "sol A").

To the dried lower phase of brain extract, sol A was added until the solution became totally soluble. For 500 gm of tissue, that usually was about 1 L solvent. That was passed over a bed of equilibrated CM SEPHADEX having a volume of 50–200 ml (about 100 ml per kg wet tissue) and allowed to elute by gravity filtration. An additional 2 L of sol A was washed through the column and the total pass-through fraction was collected and saved. The column was washed with MW (90:10) until the bed volume equilibrated (SEPHADEX would shrink slightly). Anionic lipids were eluted using a solution of 0.5M TEA in MW (90:10, titrated to a pH of 9.25 by gently bubbling $CO_2$ gas through the solvent). For 500 gm starting tissue, 500 ml of 0.5M TEA was sufficient to quantitatively elute compounds A and B. as well as sphingosine (SPN) and a compound designated "compound E." In separate tests, that concentration of TEA also eluted standard psychosine, although psychosine was absent in brain extract. Increasing the TEA concentration up to 2.0M did not result in elution of any other detectable species.

Figure 1B:
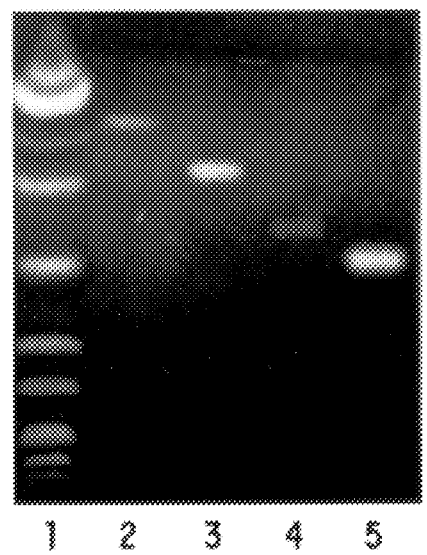

The results are shown in FIGS. 1A and 1B. In FIG. 1A, TLC was developed in chloroform-methanol-28% $NH_4OH$ (80:20:2). Bands were detected by orcinol-sulfuric acid. Lane 1, total eluate from carboxymethyl SEPHADEX column with 0.5M TEA; lane 2, purified compound A; lane 3, purified compound B; lane 4, purified compound C; and lane 5, sphingosine.

FIG. 1B is the same chromatogram as in FIG. 1B, but the bands were detected by spraying with 0.01% PRIMULINE and viewed under UV light.

FIG. 1A, which shows the pattern with orcinol-sulfuric acid, with compounds A, B and E stained purple, indicates the presence of carbohydrate. Other bands were different in coloration with orcinol-sulfuric acid reaction.

Further Purification of Compounds A and B using HPLC IATROBEAD Chromatography

The 0.5M TEA fraction from CM SEPHADEX was evaporated to dryness several times using absolute ethanol to rid the sample of TEA. The fraction was transferred to a screw-cap tube and diluted to a final volume of 2–10 ml in chloroform/methanol 2:1 and 10 $\mu$l was chromatographed on high-performance thin-layer chromatography (HPTLC) (Merck) plates in chloroform/methanol-$NH_4OH$ 80:20:2. Viewing was accomplished with hand-held UV light using either 0.8% PRIMULIN (Sigma) in 80% acetone or 30% FLUORESCAMINE (Sigma). It also was possible to detect compounds A and B with 0.5% orcinol (Sigma) in 10% sulfuric acid followed by baking in a thin-layer chromatography (TLC) oven.

To separate compounds A and B, as well as E, from the more polar sphingosines and contaminating neutral glycolipids, it was necessary to perform several HPLC gradient runs. This was accomplished using a very nonpolar IHW gradient. A long column (0.4×60 cm) packed with IATROBEADS (10 $\mu$M) first was equilibrated by washing the column according to the following scheme: at 2.0 ml/min the starting concentrations were IHW (55:40:5); the gradient was increased to IHW (55:25:20) over the next 30 minutes, followed by decreases to IHW (55:40:5) for 30 minutes, IH (60:40) for 30 minutes and finally washing with hexane (100%) for 30 minutes.

The 0.5M TEA fraction was prepared for injection by evaporating to dryness and redissolving in 100% hexane in the following manner. For a 2 ml injection, 100 $\mu$l of chloroform/methanol (2:1) was added, the cap was screwed on tightly and the sample was warmed under hot tap water to about 50° C. and sonicated. In most cases, that solubilized the lipid. To that thick oil, 2 ml of 100% hexane was added during sonication. In some cases, a very fine, opalescent precipitate formed, but never interfered with the injection.

The sample was loaded onto the column and subjected to gradient eluting at 0.5 ml/min. Gradient elution was started from the hexane to IHW 10:89:1 from 25 to 150 minutes and continued from that solvent to IHW 24:74:2 (150 to 400 minutes), to IHW 55:40:5 (400 to 500 minutes) and to IHW 55:25:20 (500 to 600 minutes). Effluent (3 ml/tube) was collected over a fraction collector in 100 tubes and the tubes were streaked for HPTLC analysis (chloroform/methanol/$NH_4OH$, 80:20:2). Fractions were pooled based on separation of three detectable compound A, B and E bands. However, sphingosine overlap made several HPTLC runs necessary in order to purify compounds A and B, as well as E, to homogeneity. In this manner, sphingosine was also conveniently purified, as well as a slower migrating sphingosine analog (FIG. 1B, lanes 4,5).

EXAMPLE 2

COMPARISON OF GRAY VS. WHITE MATTER AND CEREBELLUM VS. BRAINSTEM

Figure 2:
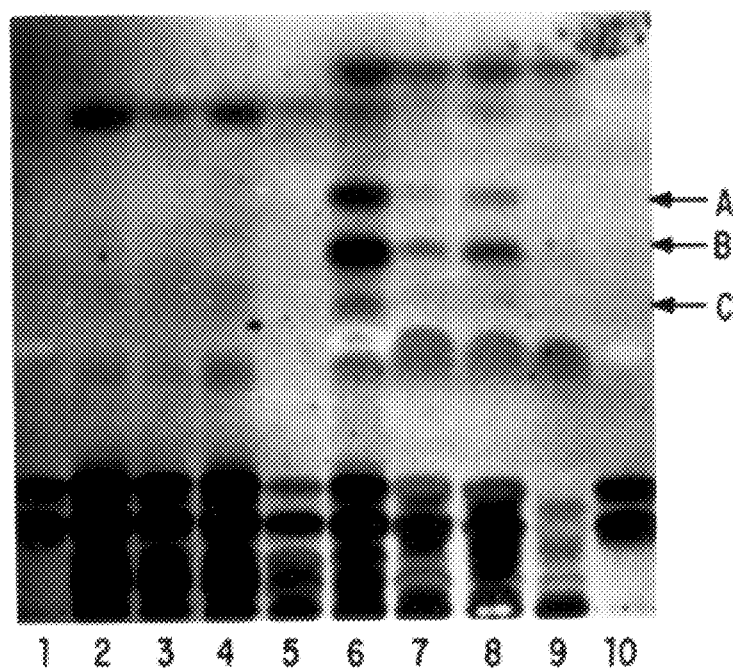
FIG. 2 is an HPTLC pattern of anionic lipid from various regions of human brain. Anionic lipids were isolated by chromatography on carboxymethyl SEPHADEX and eluted with 0.5M triethylamine and the thin layer chromatograph was developed in chloroform/methanol/$NH_4OH$ (80:20:2). Lanes 1 and 10, standard ceramide monohexoside (CMH); lane 2, lower phase from white matter; lane 3, lower phase from cerebellum; lane 4, lower phase from brain stem; lane 5, lower phase from gray matter; lane 6, 0.5M triethylamine eluate from carboxymethyl SEPHADEX column of white matter; lane 7, the same fraction as in lane 6 but prepared from cerebellum; lane 8, the same fraction as in lane 6 but prepared from brain stem; and lane 9, the same fraction as in lane 6 but prepared from gray matter.

Equal weights (100 gm) of white and gray matter from cerebrum were collected from the same human brain and processed side by side to obtain lower phases. Equal weights of cerebellum and brainstem were also obtained. These samples were passed over CM SEPHADEX as described above and eluted with 0.5M TEA. FIG. 2 shows the orcinol staining of various fractions from gray and white matter, cerebellum, and brainstem.

In FIG. 2, the lanes are as follows: lanes 1 and 10, standard CMH; lane 2, lower phase from white matter; lane 3, lower phase from cerebellum; lane 4, lower phase from brain stem; lane 5, lower phase from gray matter; lane 6, 0.5 triethylamine eluate from carboxymethyl SEPHADEX column of white matter; lane 7, the same fraction as in lane 6 but prepared from cerebellum; lane 8, the same fraction as in lane 6 but prepared from brain stem; and lane 9, the same fraction as in lane 6 but prepared from gray matter.

Lane 6 clearly shows that the major source of compounds A and B is the white matter of the cerebrum. There was no detectable amount of compounds A, B or E in cerebral gray matter, trace amounts in the cerebellum, and 10–15% (relative to cerebral white matter) in the brainstem (FIG. 2, lanes 6–9).

Further, compounds A, B and E were present in human brain white matter but undetectable in gray matter. The composition of compounds A, B and E in six different brains with different ages was measured quantitatively as described above.

EXAMPLE 3

CHEMICAL DEGRADATION OF COMPOUNDS A, B AND E

Compounds A, B and E separated on HPTLC were all stained by orcinol-sulfuric acid reaction with a color typical for neutral glysophingolipid (GLS), but were all negative with resorcinol-HCl reaction specific for gangliosides. Preliminary chemical degradation with weak acid/base treatment was performed. Weak acid treatment as catalyzed by mercuric chloride (0.1% $HgCl_2$ in 0.1N HCl) was performed according to the original method of Feulgen et al. (6); alternatively, glycolipid was treated in 0.3N HCl in MeOH at 80° C. for 30 minutes. Weak base hydrolysis was carried out in 0.3N NaOH in MeOH at 80° C. for 40 minutes.

Figure 3:
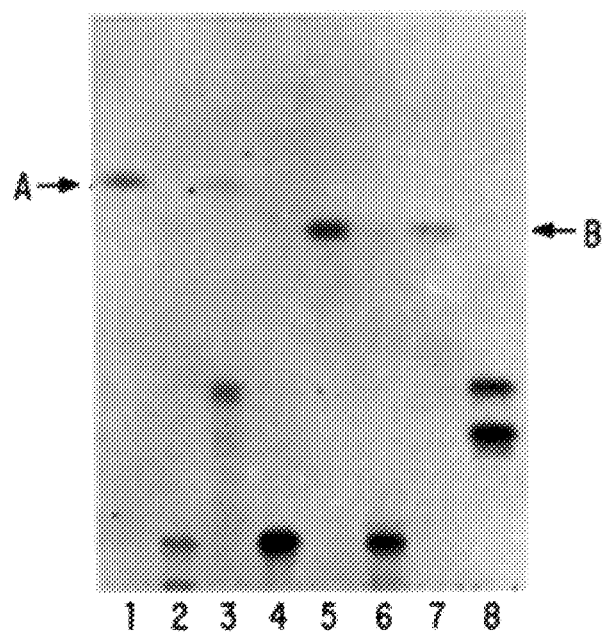
FIG. 3 is an HPTLC pattern of purified plasmalopsychosine and degradation products by weak acid and alkaline treatment: Lane 1, compound A; lane 2, compound A treated in 0.3N HCl in MeOH 80° C. 30 minutes; lane 3, compound A treated with 0.3N NaOH in MeOH, 80° C. 40 minutes; lane 4, standard psychosine; lane 5, compound B; lane 6, compound B treated in 0.3N HCl in MeOH 80° C. 30 minutes; lane 7, compound B treated in 0.3N NaOH in MeOH 80° C. 40 minutes; and lane 8, CMH.

The results are shown in FIG. 3, which is the HPTLC pattern of purified plasmalopsychosine and degradation product by weak acid and alkaline.

The lanes in FIG. 3 are as follows: lane 1, compound A; lane 2, compound A treated in 0.3N HCl in MeOH 80° C. 30 minutes; lane 3, compound A treated with 0.3N NaOH in MeOH, 80° C. 40 minutes; lane 4, standard psychosine; lane 5, compound B; lane 6, compound B treated in 0.3N HCl in MeOH 80° C. 30 minutes; lane 7, compound B treated in 0.3N NaOH in MeOH 80° C. 40 minutes; and lane 8, ceramide monohexoside (CMH).

The results show that compounds A, B and E (results not shown for compound E) could be degraded to the same position as psychosine after weak acid hydrolysis catalyzed by $HgCl_2$ in 0.1N HCl or 0.3N HCl in MeOH, but were resistant to base hydrolysis (FIG. 3, lanes 5–8).

EXAMPLE 4

STRUCTURAL CHARACTERIZATION OF COMPOUNDS A, B AND E AS PLASMALOPSYCHOSINE

Preparation of long chain enol methyl ether standards. Long chain alcohols (n-hexadecanol and n-octadecanol), purchased from Aldrich (Milwaukee, WI), were oxidized to aldehydes using pyridinium dichromate in $CH_2Cl_2$, according to the method of Corey and Schmidt (25). Identity and purity of products were verified by GC-MS. Aldehydes were converted to enol methyl ethers (EMEs) by treatment with 0.5N HCl/5M $H_2O$ in methanol at 80° C. for 5.5 hr. The methanolysate was cooled and extracted 3× with hexane. The combined hexane extracts were evaporated under $N_2$ stream at 37° C. to approximately 10 μl, then diluted with hexane for analysis by GC-MS as described below. Under these conditions, production of EME derivatives was favored over conversion to long chain dimethylacetals.

Long chain aldehyde analysis. Lipid samples (400–500 μ) were methanolyzed in 2.0 ml 0.5N HCl/5M $H_2O$ in MeOH for 5.5 hr at 80° C. The methanolysate was cooled and extracted 3× with hexane. The combined hexane extracts were evaporated under $N_2$ stream at 37° C. to approximately 10 μl, then taken up in a volume of hexane (10–50 μl) providing a suitable dilution for analysis by GC-MS. GC-MS of aliquots of the hexane extractable material were performed using a Hewlett-Packard 5890A gas chromatograph interfaced to an Extrel ELQ 400 quadrupole mass spectrometer. Gas chromatography was performed using a 30 m DB-5 (J & W Scientific, Ranch Cordova, CA) bonded-phase fused silica capillary column (0.25 mm o.d. 0.25 μm film thickness; splitless injection; temperature program, 140°–250° C. at 4° C./min). The mass spectrometer was operated in either Cl (isobutane; mass range, 150–500 u, scanned once per second) or El (mass range 50–500 u, scanned once per second) mode. EME derivatives were identified by characteristic ions and retention times compared with synthetic standards (see previous section), verified by co-injection when necessary.

Monosaccharide analysis. Lipid samples (50–100 μg) were methanolyzed in 1.0 ml 0.5N HCl in anhydrous MeOH for 24 hr at 80° C. The methanolysate was cooled and extracted 3× with hexane. The acidic MeOH lower layer was neutralized by addition of $Ag_2CO_3$ (approximately 10 mg) and treated with acetic anhydride (100 μl) for 6 hr at room temperature. Following centrifugation and removal of the MeOH, the precipitate was washed 2× with 1 ml portions of MeOH. The combined MeOH extracts were dried under $N_2$ stream. The resulting monosaccharide methyl glycosides were analyzed as their per-O-trimethylsilyl ethers (26, 27) by GC-MS using the Extrel ELQ 400 system described above (DB-5 column; splitless injection; temperature program, 140°–270° C. at 4° C./min; Cl-MS (isobutane) mode). The combined hexane extracts were evaporated under $N_2$ stream at 37° C. to approximately 10 μl, then diluted with hexane for analysis by GC-MS under the conditions described in the previous section.

Chemical derivatizations of intact lipids. Lipid samples (approximately 50 μg) were permethylated by the method of Ciukanu and Kerek (28), as modified by Larson et al (29), except that equal volumes of MeI and DMSO were used (100 μl each). The reaction time was 30 min, and MeI was removed by flushing with $N_2$ for 25 min at 37° C. prior to partitioning between $CHCl_3$ and $H_2O$. After washing 3× with $H_2O$, the $CHCl_3$ was evaporated to dryness under $N_2$.

Lipid samples were per-N,O-acetylated with 2:1 pyridine-acetic anhydride (0.5 ml, 20 hr, room temperature). The reagents were removed by flushing under $N_2$ stream at 37° C., with addition of anhydrous toluene as co-distallant. A portion of each sample was subsequently de-O-acetylated by the Zemplén procedure (brief treatment with NaOMe in anhydrous MeOH) (30).

Methylation/linkage analysis. Linkage positions of substituents on glycosyl residues were determined by permethylation of approximately 50 μg of each sample (see previous section), followed by hydrolysis, reduction, per-acetylation and GC-MS as described in detail elsewhere (22), except that the analysis was performed on the Extrel ELQ 400 GC-MS system described above (DB-5 column; splitless injection; temperature program, 140°–250° C. at 4° C./min; EI-MS mode), with identification of partially methylated alditol acetate (PMAA) derivatives made by retention time and characteristic electron-impact mass spectra (31, 32). Identifications were confirmed by comparison with PMAA's in known standard mixtures.

Fast atom bombardment mass spectrometry. FAB-MS was performed on a JEOL (Tokyo, Japan) HX-110/DA-5000 mass spectrometer/data system, operated in the accumulation mode at full acceleration voltage (10 kV); xenon beam, 6 kV; resolution, 3000. Aliquots of sample (approximately 20 μg) in MeOH were transferred to a FAB target and suspended in an appropriate matrix. For native lipid samples analyzed by FAB-MS the matrix was TEA/15-crown-5 (33, 34) and the mass range was 100–2000 u. Three scans were accumulated for each spectrum. Sodium iodide in glycerol was used as the calibration standard.

Samples of native, acid treated, per-N,O-acetylated, and per-N,O-acetylated de-O-acetylated lipids were analyzed by $^+$FAB-MS using NBA matrix, with and without addition of sodium acetate. Other conditions were the same as above. KI/CsI was used as the calibration standard.

Methanolysis: monosaccharide analysis. Since the unknown lipids could be stained with orcinol, indicating the presence of some carbohydrate component, they were subjected to monosaccharide analysis, by GC-MS of trimethysilyl methyl glycosides produced following acidic methanolysis. In each case, peaks were observed for the usual trimethylsilyl derivatives of galactose (data not shown). No other saccharide peaks were observed, except for a trace (<1%) of glucose detected in the methanolysate of the uppermost band.

Methanolysis: analysis of fatty aldehydes. GC-MS analysis of the hexane wash, following acidic methanolysis, normally is used for determination, as methyl esters, of the fatty acyl components of glycosphingolipids, in general those attached to sphingosine to make up the ceramide moieties. In the instant case, no fatty acid methyl esters were detected in any of the lipid fractions analyzed. A number of unknown peaks were observed. Following evaluation of the results of FAB-MS analysis of the intact lipids (described below), the identity of the peaks was determined, and several major components found to correspond to long chain enol methyl ethers. Two components were found to be identical in retention times and mass spectra to enol methyl ethers prepared by acidic methanolysis of authentic 16:0 and 18:0 long chain aldehydes. Two other components, having molecular weights 2 amu less than those synthesized from the 18:0 aldehydes, and having slightly faster retention times, were assumed to correspond to isomeric unsaturated 18:1 species. The four components are identified as provided in the GC-MS reproduced in FIGS. 4A and 4B.

FIGS. 4A and 4B are the results of gas chromatography-chemical ionization/mass spectrometry (GC-CI/MS) of long chain methyl enol ethers. FIG. 4A shows the results from methanolysis of the middle band lipid; FIG. 4B shows the results from methanolysis of standard n-16:0 and −18:0 aldehydes. Peaks were identified as 1: 16:0; 2a and 2b: isometric 18:1; and 3: 18:0 methyl enol ethers, having pseudomolecular ion masses of 255, 281, and 283 u, respectively. Peaks marked by an asterisk are impurities common to both samples, probably arising from the derivatization reagents.

FAB-MS analysis of native lipids. FAB mass spectra of the unknown native lipids were obtained in both positive and negative ion modes (7–9) and the results are shown in FIGS. 5A to 5D.

FIG. 5 shows FAB-MS of native lipids: FIG. 5A, $^+$FAB mass spectrum of upper band lipid in 3-nitrobenzyl alcohol (NBA) matrix; FIG. 5B, $^+$FAB mass spectrum of middle band lipid in NBA matrix; FIG. 5C, $^+$FAB mass spectrum of middle band lipid in NBA/sodium acetate matrix; FIG. 5D, $^-$FAB mass spectrum of middle band lipid in TEA/15-crown-5 matrix.

Figure 5A:
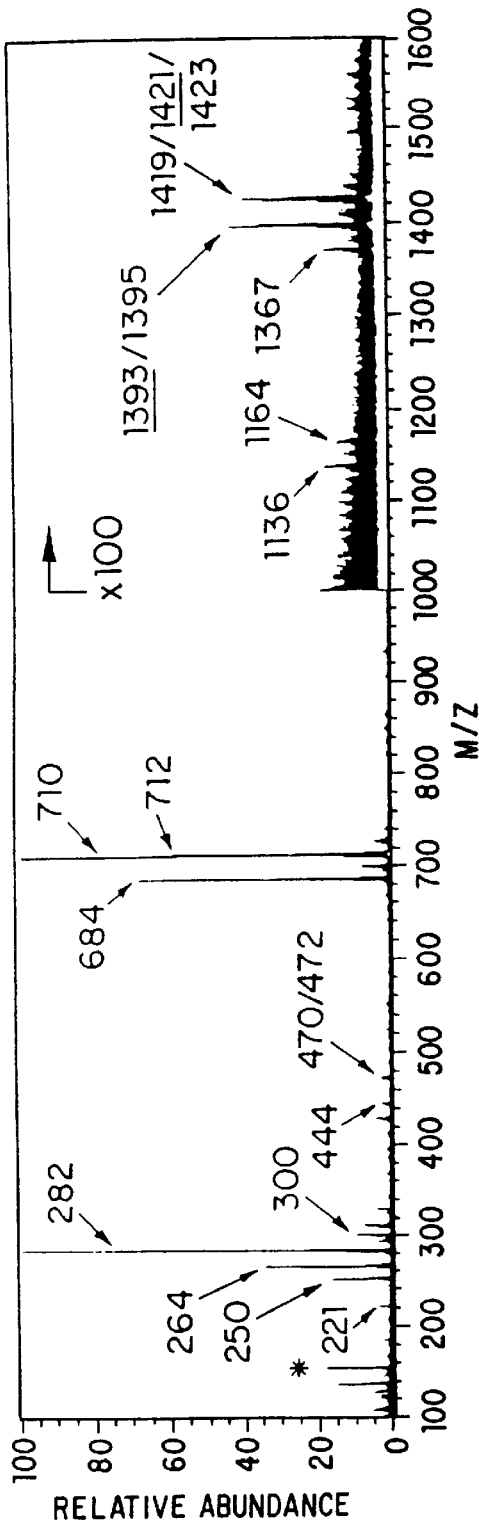
FIGS. 5A to 5D are the data from fast atom bombardment-mass spectrometry (FAB-MS) of native lipids.
Figure 5B:
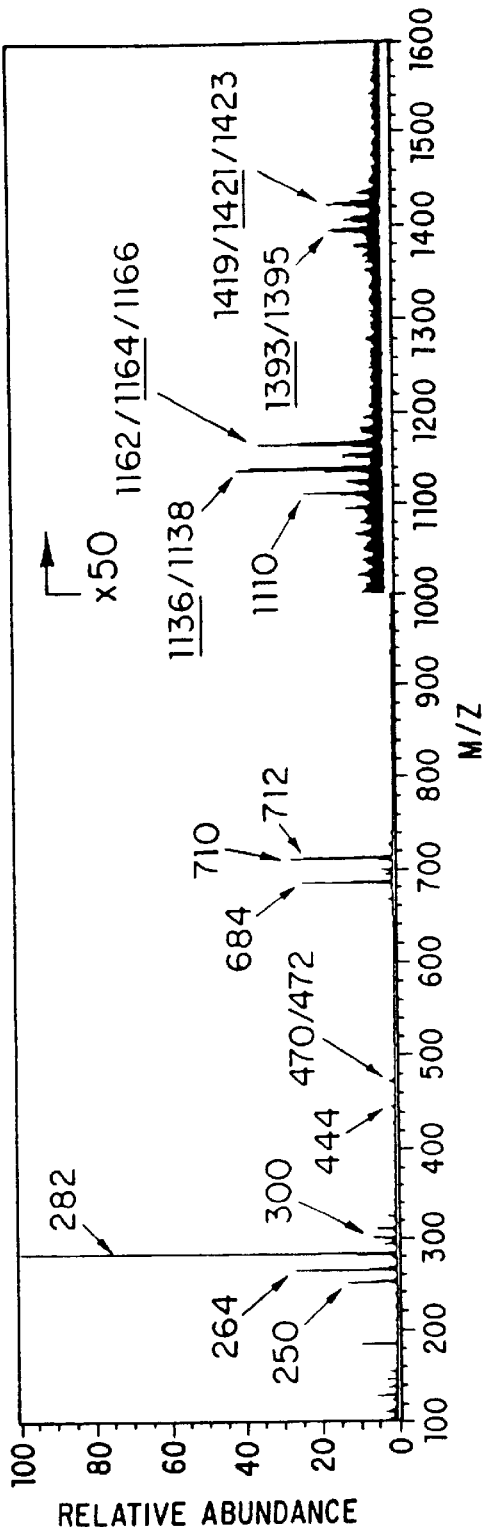
Figure 5C:
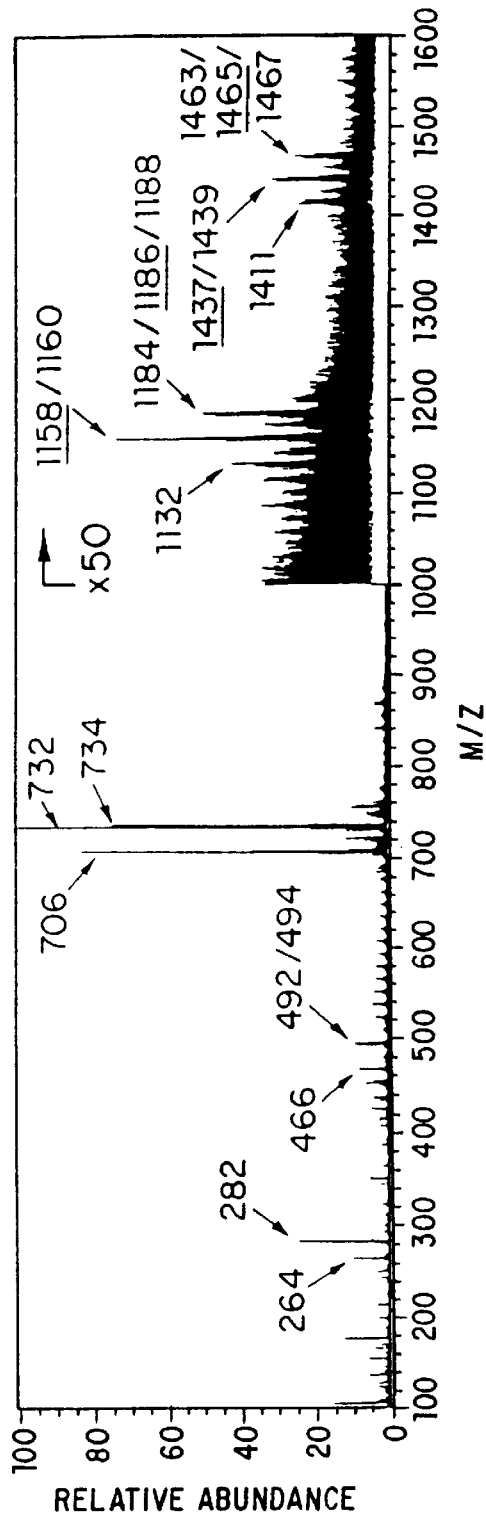

The positive ion spectra of the upper and middle (HPTLC) bands are reproduced in FIGS. 5A and 5B. Observed in both spectra were prominent ions at m/z 684, 710, and 712 (nominal, monoisotopic masses). That these corresponded to pseudomolecular ions [MH]$^+$ was confirmed by obtaining spectra following addition of sodium acetate to the matrix. Sodiated molecular ions were then observed at m/z 706, 732, and 734 (see FIG. 5C). Further confirmation was provided by negative ion spectra, in which mode pseudomolecular ions [M–H]$^-$ could be observed at m/z 682, 708, and 710 (see FIG. 1D). Since the ions correspond to the odd molecular weights 683, 709, and 711 Da, it could be concluded that each species contains an odd number of nitrogen atoms. Interestingly, the negative ion spectra was characterized by the presence of extra peaks apparently associated with the pseudomolecular ions. Each pseudomolecular ion is accompanied by an ion at m/z [M–H+42], along with a less abundant one at m/z [M–H+26]. Such adduct ions were previously observed in the negative ion spectra of semisynthetic lyso- and de-N-acetyl gangliosides only when TEA was used as the matrix (1,2). They have been observed only with compounds containing a free amino group and are believed to result from an addition reaction with some component in the matrix, either present as an impurity, or formed by decomposition of TEA under the conditions of fast atom bombardment (2). In that case, the conclusion that the lipids bear a primary amino function is consistent with detection by fluorescamine on HPTLC plates.

Figure 5D:
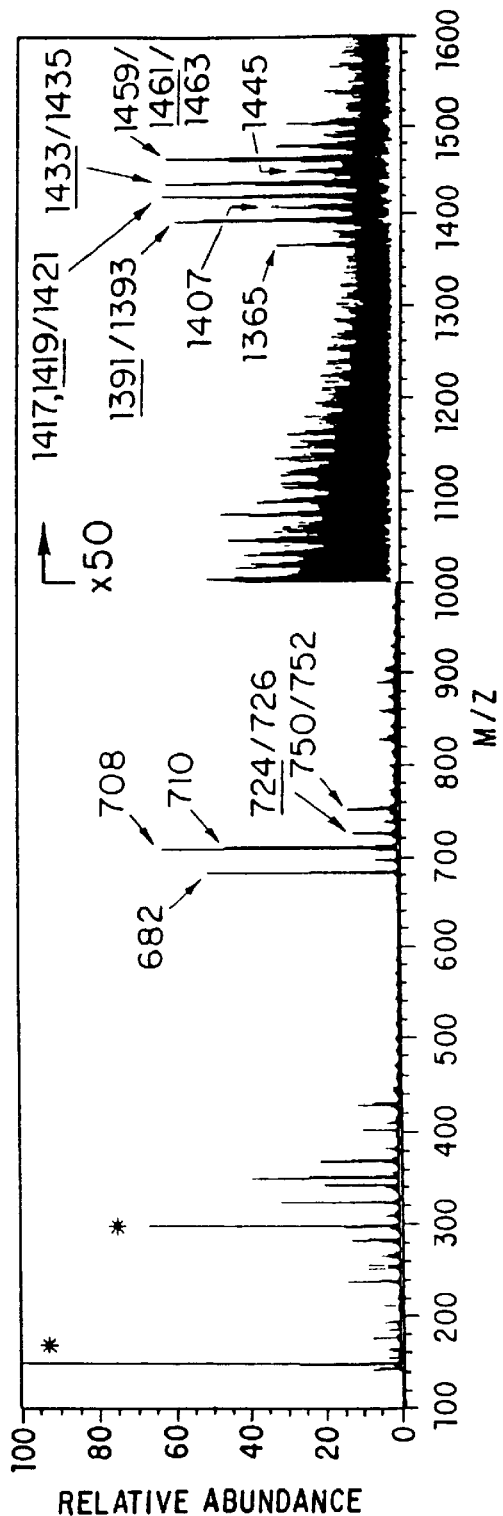

Of some further interest was the observation in the positive ion spectra, of peaks consistent with dimeric ions. Those were found between 1300 and 1500 u at masses corresponding to the possible combinations of the monomeric species, i.e., at m/z [M$_1$+M$_2$+H]$^+$ and [M$_1$+M$_2$–H+2Na]$^+$ (see FIGS. 5A, 5B and 5C). In the negative ion spectra, they were accompanied, again, by adduct ions 26 and 42 u to higher mass (FIG. 5D). Such noncovalent self-associations of glycolipids in FAB spectra have not been reported, although Ballou and Dell (23) studied the interaction between long chain alkyl trimethylammoniun ions and a natural 3-methyl-mannose polymer from *Mycobacterium smegmatitis* by $^+$FAB-MS. In the positive ion spectra, a second set of ions, observed between 1100 and 1200 u (FIGS. 5A, 5B and 5C), may correspond to loss of a portion of one molecule in the dimeric species, although the exact nature of the loss is not clear at this time. Since the change represents the loss of an odd mass fragment (257 u), one may assume that it is a portion of a sphingosine chain including the nitrogen atom that is cleaved off.

The differences in mass between the observed pseudomolecular ions (26 and 28 u) suggested a difference in structure corresponding to a two-carbon alkyl chain, with predominant monounsaturation in the heavier homolog. Since the upper and middle bands yielded qualitatively similar spectra, it was further inferred that a structural isomerism was responsible for the difference in R$_f$ between them. In both cases, the major fragment ion in the positive mode was observed at m/z 282, associated with less abundant ions at m/z 250, 264, 300, and 310. The ions at m/z 300, 282, and 264 were previously observed by Hara and Taketomi (24) to be characteristic fragments of unsaturated d18:1 sphingosine in positive mode FAB spectra of psychosines (representing, for galactopsychosine, for example, [M+H–Gal]$^+$, [M+H–Gal–H$_2$O]$^+$, and [M+H–Gal–2H$_2$O]$^+$, respectively). Confirmation of the unknown lipids as derivatives of psychosine, and of the possible isomeric relationship between them was provided by degradative experiments monitored by FAB-MS.

Figure 6A:
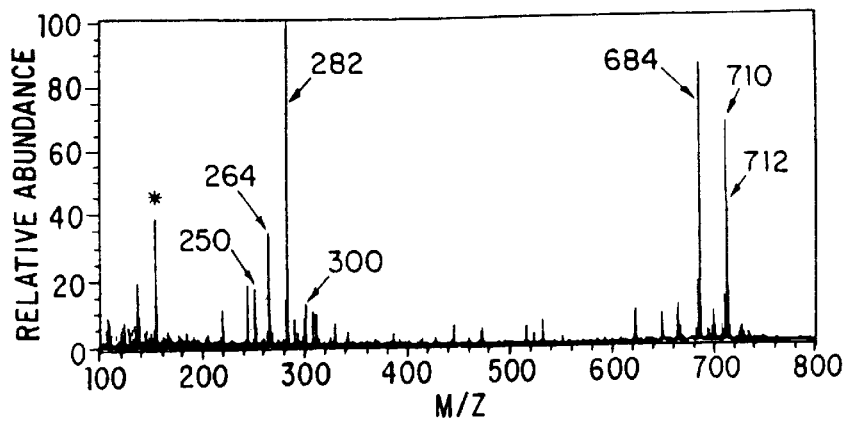
FIGS. 6A–6D are data from $^+$FAB-MS of products of treatment with $HCl/HgCl_2$: Matrix: NBA.
Figure 6B:
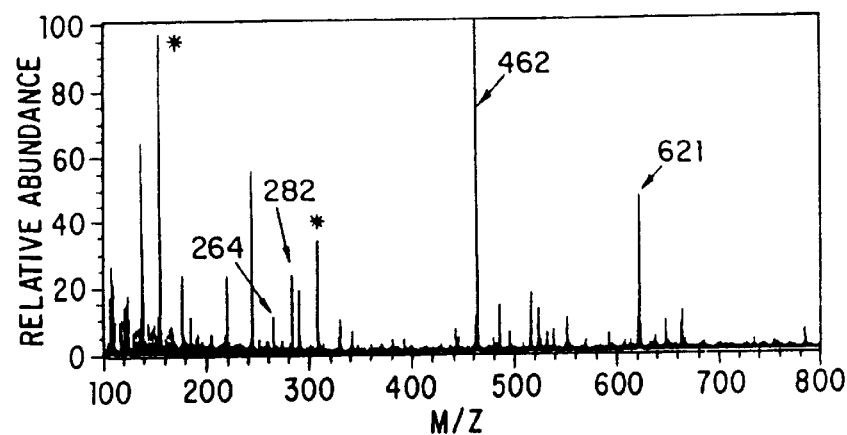
Figure 6C:
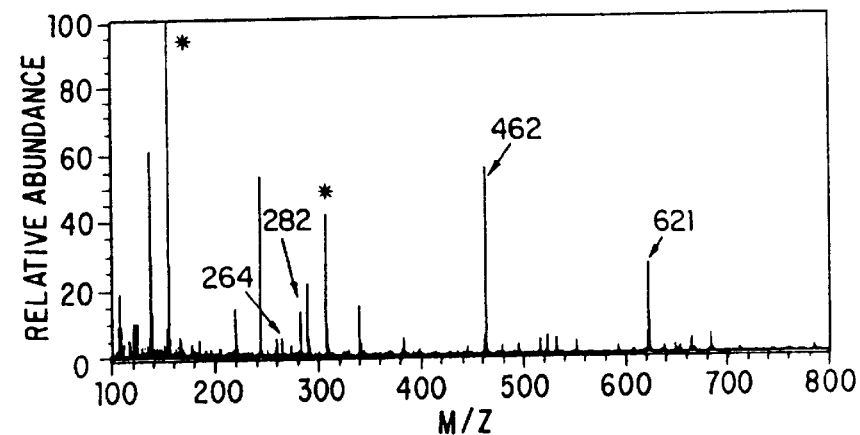
Figure 6D:
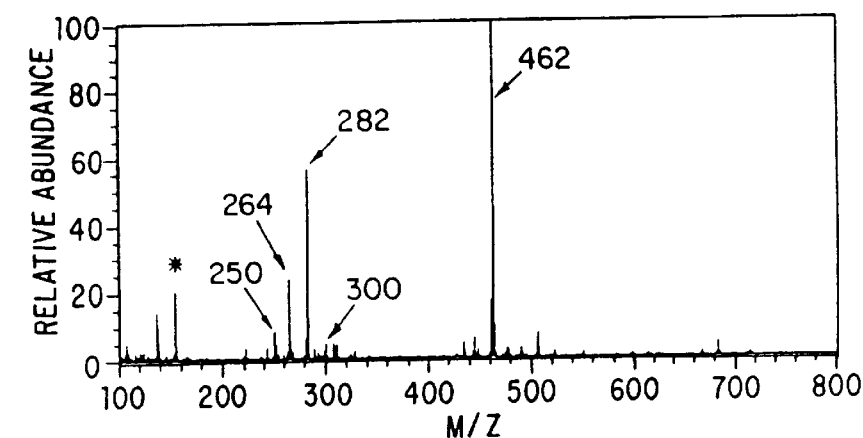

FAB-MS of the products of mild acid hydrolysis. Brief treatment of the upper band lipid with 0.1N HCl/HgCl$_2$ yielded a product whose R$_f$ was identical to that of the middle band on HPTLC. The $^+$FAB mass spectrum of this product (FIG. 6A) was virtually identical to those of the native untreated upper or middle band lipids, demonstrating an acid catalyzed transformation of the upper to the middle band lipid. On more extended treatment of the upper band, or treatment of the middle band, a new product was observed, having an R$_f$ identical to that of authentic galactopsychosine. The $^+$FAB mass spectra of these products were virtually identical to those obtained for galactopsychosine (FIGS. 6B, 6C and 6D).

FIG. 6 shows $^+$FAB-MS of products of treatment with HCl/HgCl$_2$: Matrix: NBA. A, upper band lipid, following brief acid treatment, resulting in conversion to middle band lipid; B, upper band lipid following extended acid treatment; C, lower band lipid following extended acid treatment; D, d18:1 galactopsychosine standard.

Because the lipids are newly isolated covalent modifications of psychosine, the following further conclusions can be reached. Given the great relative abundance of the ion at m/z 282 (in FIGS. 5A and 5B) compared with that at m/z 310 (which may represent a homolog containing d20:1 sphingosine), it is apparent that the differences in mass of the pseudomolecular ions must be due largely to differences in mass of the modifying group(s), rather than to the occurrence of different sphingosine chain lengths. The modifying groups would have to be such as to add incremental masses of 222, 248, and 250 u to that of the psychosine. Identical differences in mass were also observed in a series of low abundance fragments (m/z 444, 470, 472), found in the spectra of the native lipids (FIGS. 5A and 5B), which could be analogs of the fragment found at m/z 222 in the FAB mass spectrum of psychosines (24) (see FIG. 6D), but which is concomitantly eliminated from the spectra of the native modified lipids. Interestingly, a pair of fragments found at m/z 250 and 252 in the spectrum of psychosines (24) (see FIG. 6D) were also found in the spectra of the native modified lipids (FIGS. 5A and 5B), while there was no set of ions observed with masses incrementally increased as found for the m/z 222 fragment. Coincidentally, the differences in mass correspond to the differences in chain length of the enol methyl ethers found by GC-MS of the hexane soluble methanolysis products, suggesting that these might be chemical transformants of the modifying groups in question. Previously, the structure of a plasmalogen-like form of glycosphingolipid was proposed by Kochetkov et al. (13), in which the 3-OH group of psychosine was modified by attachment of a long-chain enol ether. However, in the total absence of any fragments corresponding to loss of the hexose moiety, as commonly observed in FAB mass spectra of glycosphingolipids (such as psychosine), it seemed more likely that the modifying group(s) must be attached to the galactose residue, rather than to the sphingosine moiety. The idea that these modifications might take the form of enol ethers was also shown to be erroneous by further derivatization experiments followed by FAB-MS.

FAB-MS of sequentially per-N0-acetylated and de-O-acetylated lipids. Peracetylation of the native lipids with acetic anhydride/pyridine resulted in incorporation of four acetate groups, as illustrated in FIGS. 7A, 7B and 7C.

Figure 7A:
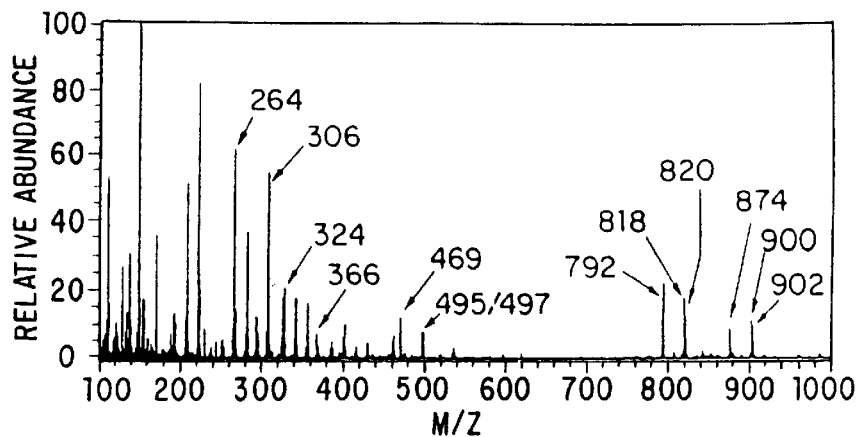
FIGS. 7A–7D are data from $^+$FAB-MS of products of acetylation/deacetylation.
Figure 7B:
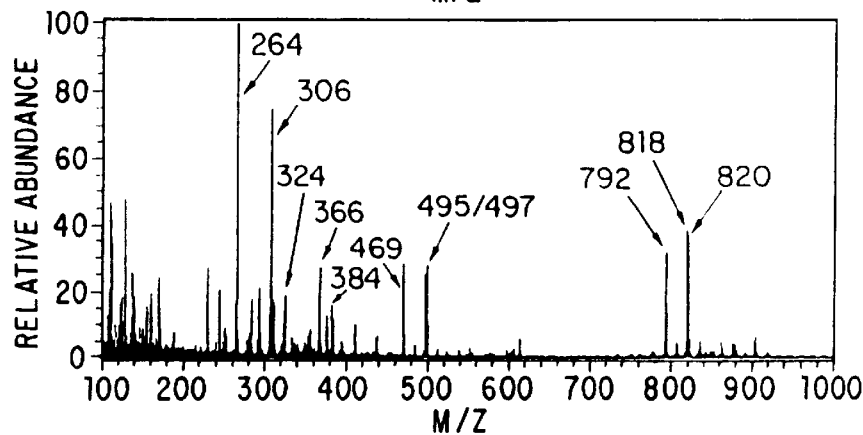
Figure 7C:
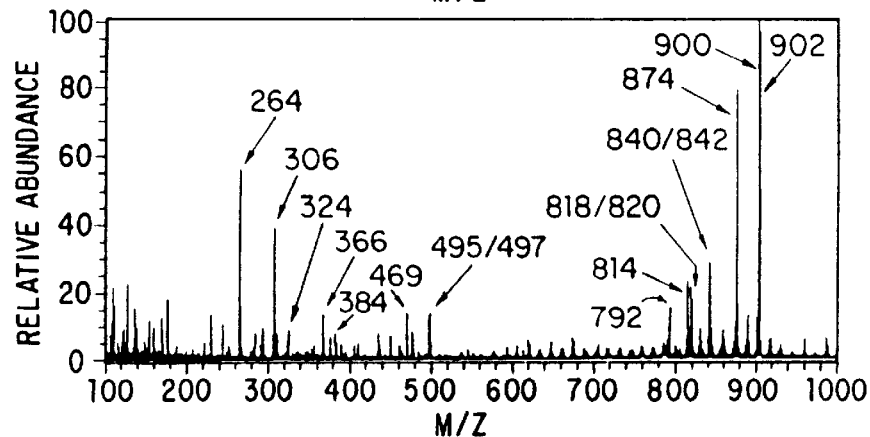
Figure 7D:
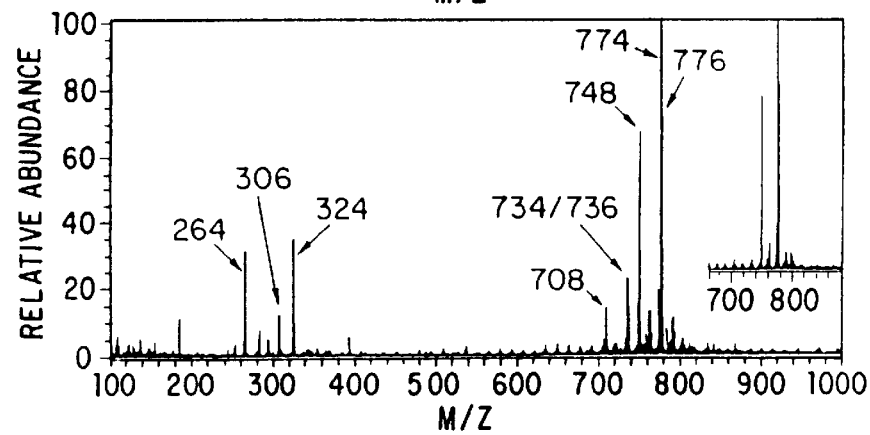

FIG. 7A is peracetylated upper band lipid in NBA matrix; FIG. 7B is peracetylated middle band lipid in NBA matrix; FIG. 7C is peracetylated middle band lipid in NBA/sodium acetate matrix; FIG. 7D is peracetylated and de-O-acetylated middle band lipid in NBA matrix (inset: same product in NBA/sodium acetate matrix, showing no change in masses of pseudomolecular ions).

For the upper lipid (FIG. 7A), pseudomolecular ions [M+Na]$^+$ at 874, 900, and 902 corresponded to the addition of 4×42 u to each of the native species. In addition, ions at m/z 792, 818, and 820 were observed, representing [MH–60]$^+$, a facile neutral loss of HOAc. Confirmation of the higher mass group as being the true pseudomolecular ions was confirmed by addition of sodium acetate to the matrix, as illustrated for the per-acetylated middle band lipid (FIG. 7C). A concomitant suppression of the [MH–60]$^+$ ions was observed under this condition. At the lower end of the spectra, the triply unsaturated (doubly dehydrated) ion m/z 264 was now the predominant sphingosine fragment. Also observed was an ion at m/z 366, probably representing a single dehydration of the N-Ac, O-Ac sphingosine fragment (m/z 384). The sphingosine fragment can eliminate one and two molecules of HOAc, to yield the ions at m/z 324 and 264, respectively. Elimination of HOAc from the fragment at m/z 366 yields the ion at m/z 306. The origin of the group of odd-mass ions, m/z 469, 495, and 497, is unclear at this time.

As illustrated for the middle band lipid (FIG. 7D), de-O-acetylation with MeONa/MeOH resulted in the loss of three O-Ac groups, and retention of one N-Ac, confirming again the presence of a reactive amine in the native lipid. Sodiated molecular ions were now observed at m/z 748, 774, and 776. Sphingosine ions were again observed at m/z 324, 306, and 264, representing the singly dehydrated, mono-N-acetylated fragment, the doubly dehydrated, mono-N-acetylated fragment, and the elimination of HOAc from the singly dehydrated fragment, respectively. The dehydrated N-Ac, O-Ac ion at m/z 366 was no longer observed. Similar results were obtained for the upper band lipid (not shown).

These results establish that (a) the 3-OH group of sphingosine is free in the native lipids and (b) the modifying group(s) occupy two hydroxyl positions on the galactose moiety. This could not be accommodated by the attachment of two enol ethers in tandem, since the mass increases relative to free psychosine would have to be twice those observed. The only modification consistent with the FAB-MS and other data appeared to be attachment of long chain aldehydes as cyclic acetals. Acetylation of d18:1 sphingosine with 16:0, 18:1, and 18:0 fatty aldehydes would yield the observed molecular weights for the new lipids. This conclusion was confirmed by methylation/linkage analysis, as described below.

Methylation analysis by GC-MS. Following permethylation, acid hydrolysis, reduction, and acetylation of the native lipids, the resulting partially methylated hexitol acetates were analyzed by GC-MS (FIGS. 8A and 8B).

Figure 8A:
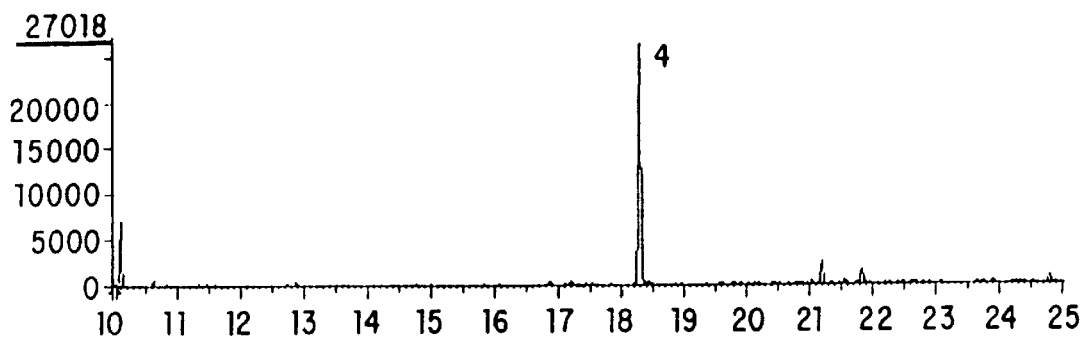
FIGS. 8A–8D are data from GC-MS analysis of partially methylated alditol acetates (PMAA's) from permethylation, hydrolysis, reduction, and acetylation of lipids.
Figure 8B:
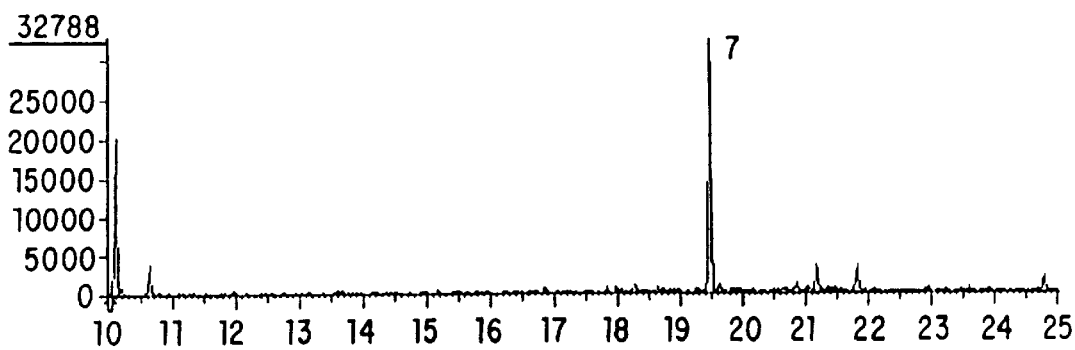
Figure 8C:
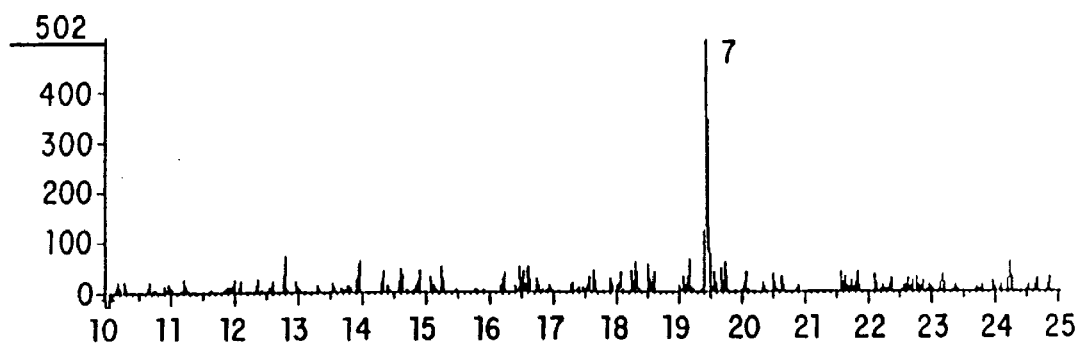
Figure 8D:
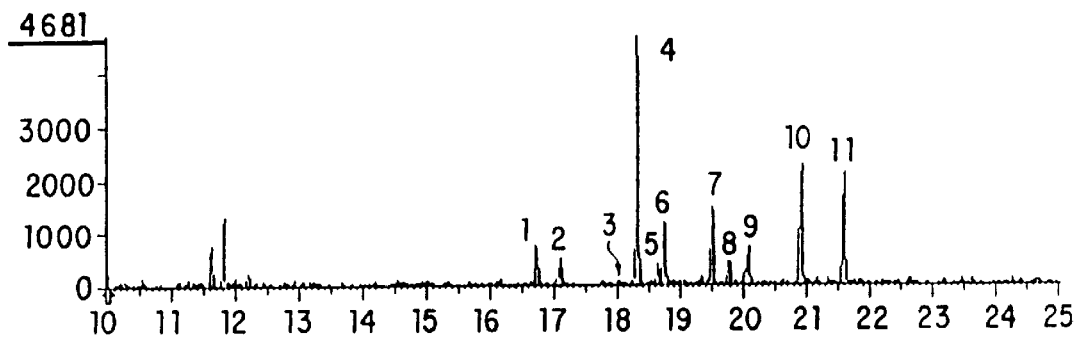

FIG. 8A is PMAA from upper band lipid; FIG. 8B is PMAA from middle band lipid; FIG. 8C is PMAA from upper band lipid following brief acid treatment; FIG. 8D is standard galactose PMAAs. Peaks are identified as PMAAs of 1: 2,3,6-tri-O-; 2: 3,4,6+2,4,6-tri-O-; 3: 2,3,4-tri-O-; 4: 2,6-di-O-; 5: 4,6-di-O-; 6: 3,6-di-O-; 7: 2,3-di-O-; 8: 6-mono-O-; 9: 3,4-di-O-; 10: 2-mono-O-; and 11: 3 (or 4)-mono-O-Me-Gal.

From the upper band lipid, 2,6-di-O-Me-Gal was obtained, while 2,3-di-O-Me-Gal was obtained from the middle band lipid. These represent 3,4- and 4,6-linked galactose moieties, respectively and show that the lipids must be isomeric cyclic acetals derived from psychosine, that in the upper band forming a five membered ring, and that in the middle band forming a six membered ring. The product from limited acid treatment of the upper band also yielded 2,3-di-O-Me-Gal (FIG. 8C), demonstrating the facile isomerization of the five-membered ring into the more stable six-membered ring. Finally, while the chiralities at the acetal C-1 positions have not definitively been determined, they are believed to be an equatorial orientation for the long chain in the six-membered acetal ring, and a pseudoequatorial orientation for this group in the five-membered ring.

EXAMPLE 5

ISOLATION AND PURIFICATION OF COMPOUNDS C AND D

Galactosyl cerebroside and sulfatide used in the examples were purchased from Sigma Chemical Co. Fatty aldehyde (plasmal) was purchased from Aldrich.

Isolation of "Fast Migrating Component"

Human brain cerebroside fraction was obtained by homogenization of brain tissue with five volumes (i.e., five times volume/weight of wet tissue) of isopropanol/hexane/water (IHW) 55:25:20 (v/v/v) and filtration through a Büchner funnel (hereinafter, all solvent ratios are by volume). The residue was subjected to rehomogenization in the same volume of the same solvent. The extract was pooled, evaporated to dryness, and subjected to Folch partition using 1 L of chloroform/methanol (CM) 2:1 and 166 ml water per 100 g original wet weight of tissue. The lower phase was repartitioned two additional times with "theoretical upper phase" (chloroform/methanol/water with 0.2% KCl 10:10:1). The resulting lower phase was evaporated to complete dryness. A large column (bed volume 1 L per 1 kg original tissue) of FLORISIL (a mixture of magnesium oxide and silicic acid gel) (from Sigma; mesh 60–100) was prepared and equilibrated in pure hexane (Burdiack & Jackson Chemical Co.). The dried lower phase was suspended in hexane (1 L per 200 g original tissue), passed over the FLORISIL column and washed with 4 L of hexane. The FLORISIL column was then eluted with 2 L of hexane/dichloroethane (DCE) 2:1, then with 2 L of DCE, and finally with 1 L of DCE/acetone 1:1. The final eluate contained acid-labile fast-migrating component.

Detection of acid-labile glycolipids

Acid-labile glycolipids were detected by hydrolysis of samples in methanol-aqueous 0.1N HCl (1,:1, v/v) heated at 90° C. for 10 min, followed by Folch partitioning and TLC examination of lower phase. The glycolipid with high TLC mobility converting to the same mobility as normal cerebroside by this treatment was regarded as the acid-labile cerebroside. Cerebroside and ester cerebrosides did not show altered TLC mobility under these conditions.

Figure 11:
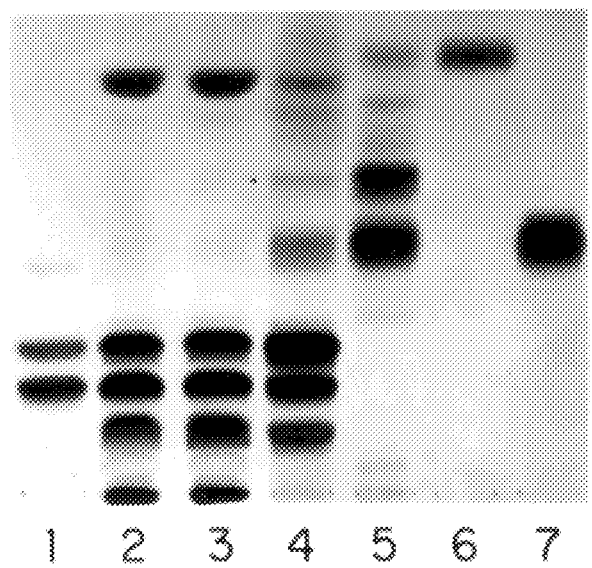
FIG. 11 is a high-performance thin-layer chromatography (HPTLC) pattern of various non-polar glycosphingolipids from Folch's lower phase prepared from human brain. The chromatograph was developed in a solvent mixture of chloroform-methanol-28% $NH_4OH$ (80:20:2 by volume). Lane 1, standard cerebroside (CMH); lane 2, lower phase obtained on Folch's partition; lane 3, unabsorbed pass through of total lower phase by carboxy-methyl SEPHADEX; lane 4, Fr. VI obtained from FLORISIL column eluted by dichloroethane-acetone (1:1, by volume); lane 5, Fraction 47–58 eluate from IATROBEAD chromatography; lane 6, purified plasmal cerebroside from Fraction 47–58; and lane 7, purified compounds C and D.

Isolation and preliminary characterization of acid-labile glycosphingolipids present in the fast-migrating fraction The acid-labile fast-migrating glycolipid was found in the unabsorbed fraction of brain extract on carboxymethyl-SEPHADEX and diethylaminoethyl-SEPHADEX of the Folch's lower phase as well as in the DCE-acetone 1:1 eluate fraction on chromatography over FLORISIL. This component was further purified by high-performance liquid chromatography (HPLC) on an IATROBEAD column loaded in pure hexane and eluted with a gradient to IHW 55:40:5 at 1 ml/min for 3 hours. Fractions were collected into 200 tubes. The acid-labile glycolipid component was eluted in tube Nos. 130–154. The pooled fraction (called fraction VI) was considered to contain most of the acid-labile glycolipid and was free of cerebroside and ester cerebrosides. The fraction VI was further purified by IATROBEADS chromatography, loaded on the columns in pure hexane and subjected to a gradient up to isopropanol/hexane (IH) 30:70. The fraction VI A (FIG. 11, lane 5), thus obtained, was further purified on a long IATROBEAD column (0.5×100 cm) with a gradient, loaded with pure hexane, and gradient eluted to IHW 50:40:5 for 3 hours. Alternatively, the compound was purified by preparative thin layer chromatography (TLC). The homogeneous band obtained is shown in FIG. 11, lane 6. On TLC, the compound migrated faster than cholesterol which migrated faster than ester cerebrosides. The compound did not contain sulfate or sialic acid which are known to be acid-labile.

FIG. 11 is a high-performance thin layer chromatography (HPTLC) pattern of various non-polar glycosphingolipids from Folch's lower phase prepared from human brain. The chromatogram was developed in a solvent mixture of chloroform/methanol/28% $NH_4OH$ (80:20:2). Lane 1 is standard CMH (cerebroside); lane 2 is lower phase obtained on Folch's partition; lane 3 is unabsorbed pass through of total lower phase by carboxymethyl-SEPHADEX; lane 4 is Fr. VI obtained by FLORISIL column (eluted by dichloroethane/actone (1:1, by volume); lane 5 is Fraction 47–58 eluate on IATROBEAD chromatography; lane 6 is purified plasmal cerebroside from Fractions 47–58; and lane 7 is purified ester-cerebrosides.

EXAMPLE 6

CHEMICAL DEGRADATION OF COMPOUNDS C AND D

Compounds C and D, as well as cerebroside (CMH), were chemically degraded with an acid or base treatment. Acid treatment was in 0.3N HCl in MeOH at 80° C. for 30 minutes. Weak base hydrolysis was carried out in 0.3N NaOH in MeOH at 80° C. for 40 minutes. The compounds and their degradation products were then separated by high-performance thin-layer chromatography. The results are shown in FIG. 12.

Figure 12:
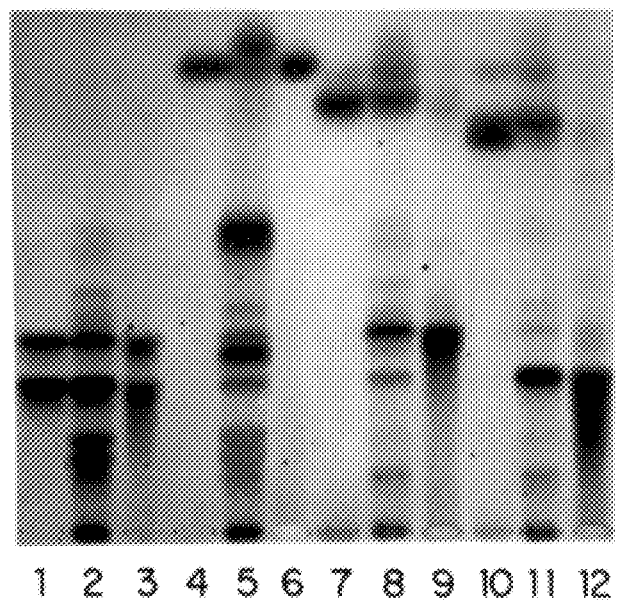
FIG. 12 is an HPTLC pattern of cerebroside (CMH), plasmalocerebrosides C and D and ester cerebroside and their degradation pattern with weak acid and weak base: Lane 1, CMH; lane 2, CMH degraded by 0.3N HCl MeOH; lane 3, CMH treated with 0.3N NaOH; lane 4, plasmalocerebroside; lane 5, plasmalocerebroside treated with 0.3N HCl in MeOH; lane 6, plasmalocerebroside treated with 0.3N NaOH in MeOH; lane 7, ester cerebroside 1; lane 8, ester cerebroside 1 treated with 0.3N HCl in MeOH; lane 9, ester cerebroside 1 treated with 0.3N NaOH in MeOH; lane 10, ester cerebroside 2; lane 11, ester cerebroside 2 treated with 0.3N HCl in MeOH; and lane 12, ester cerebroside 2 treated with 0.3N NaOH in MeOH.

In FIG. 12, the lanes are as follows:

Lane 1, CMH; lane 2, CMH degraded by 0.3N HCl in MeOH; lane 3, CMH 0.3N NaOH; lane 4, plasmalocerebroside; lane 5, plasmalocerebroside treated with 0.3N HCl in MeOH; lane 6, plasmalocerebroside treated with 0.3N NaOH in MeOH; lane 7, ester cerebroside 1; lane 8, ester cerebroside 1 treated with 0.3N HCl in MeOH; lane 9, ester cerebroside 1 treated with 0.3N NaOH in MeOH; lane 10, ester cerebroside 2; lane 11, ester cerebroside 2 treated with 0.3N HCl in MeOH; and lane 12, ester cerebroside 2 in 0.3N NaOH in MeOH.

The results show that the plasmalocerebroside are acid-labile and base stable, whereas the cerebroside esters in lane 7 and 10 are essentially acid resistance.

EXAMPLE 7

STRUCTURAL CHARACTERIZATION OF COMPOUNDS C AND D

Fatty acid, aldehyde and monosaccharide analysis. Fatty acids were estimated as methylesters (FAMEs) liberated by methanolysis (1.0 ml 0.5N HCl in anhydrous methanol, 80° C., 24 hr) of about 30–50 µg of lipid. Fatty aldehydes released during the same procedure were converted to long chain enol methyl ethers (EME's) as described for the psychosine fatty acetals). Both of the components were extracted from the methanolysate, prior to neutralization, by partitioning 3× with approximately equal volumes of hexane. The combined hexane extracts were reduced in volume under N$_2$ stream at 35°–40° C. to approximately 1–2 µl, then taken up in a volume of hexane (10–50 µl) providing a suitable dilution for analysis by GC-MS. GC-MS of aliquots of the hexane extractable material were performed using a Hewlett-Packard 5890A gas chromatograph interfaced to an Extrel ELQ 400 quadrupole mass spectrometer. Gas chromatography was performed using a 30 m DB-5 (J & W Scientific, Ranch Cordova, Calif.) bonded-phase fused silica capillary column (0.25 mm o.d., 0.25 µm film thickness; splitless injection; temperature program, 150°–290° C. at 4° C./min). The mass spectrometer was operated in either CI (isobutane; mass range, 150–500 u, scanned once per second) or EI (mass range 50–500 u, scanned once per second) mode. Derivatives were identified by characteristic ions and retention times, verified by coinjection with standards when necessary.

The remaining acidic MeOH lower layer was neutralized by addition of Ag$_2$CO$_3$ (approximately 10 mg) and treated with acetic anhydride (100 µl) for 6 hr at room temperature. Following centrifugation and removal of the MeOH, the precipitate was washed 2× with 1 ml portions of MeOH. The combined MeOH extracts were dried under N$_2$ stream. The resulting monosaccharide methyl glycosides were anlayzed as their per-O-trimethylsilyl ethers (26, 27) by GC-MS using the Extrel ELQ 400 system described above (DB-5 column; splitless injection; temperature program, 140°–270° C. at 4° C./min; CI-MS (isobutane) mode).

Methylation/linkage analysis. Linkage positions of substituents on glycosyl residues were determined by permethylation of approximately 50 µg of each sample, followed by hydrolysis, reduction, peracetylation and GC-MS as described in detail elsewhere (22), except that the analysis was performed on the Extrel ELQ 400 GC-MS system described above (DB-5 column; splitless injection; temperature program, 140°–250° C. at 4° C./min; EI-MS mode), with identification of partially methylated alditol acetate (PMAA) derivatives made by retention time and characteristic electron-impact mass spectra (31,32). Identifications were confirmed by comparison with PMAA's in known standard mixtures.

Fast atom bombardment mass spectrometry. $^+$FAB-MS was performed on a JEOL (Tokyo, Japan) HX-110/DA-5000 mass spectrometer/data system, operated in the accumulation mode at full acceleration voltage (10 kV); xenon beam, 6 kV; mass range, 3000; resolution, 3000. Aliquots of sample (approximately 20 µg) in MeOH were transferred to a FAB target and suspended in NBA matrix. Three scans were accumulated for each spectrum. Kl/Csl was used as the calibration standard.

Identification of fatty aldehyde and fatty acid by GC-MS after methanolysis. The acid-labile compounds gave a "plasmal reaction" under classical conditions indicating the presence of plasmal. That was confirmed by GC-MS analysis after methanolysis.

GC-MS analysis of hexane extract of HCl-methanolysate revealed the presence of multiple peaks which were not detected in the methanolysate of normal cerebroside or ester cerebroside in addition to those peaks corresponding to fatty acid methyl esters (FAMEs) 16:0, 18:1, 18:0, and 24:1. The peaks were determined by comparison of retention times along with electron impact (EI) and chemical ionization (CI) mass spectra to authentic compounds. They were thus identified as enol methyl ethers (EME's) derived from fatty aldehyde, i.e., as EMEs of 16:0, 18:0 and 18:1 (FIG. 13).

Figure 13:
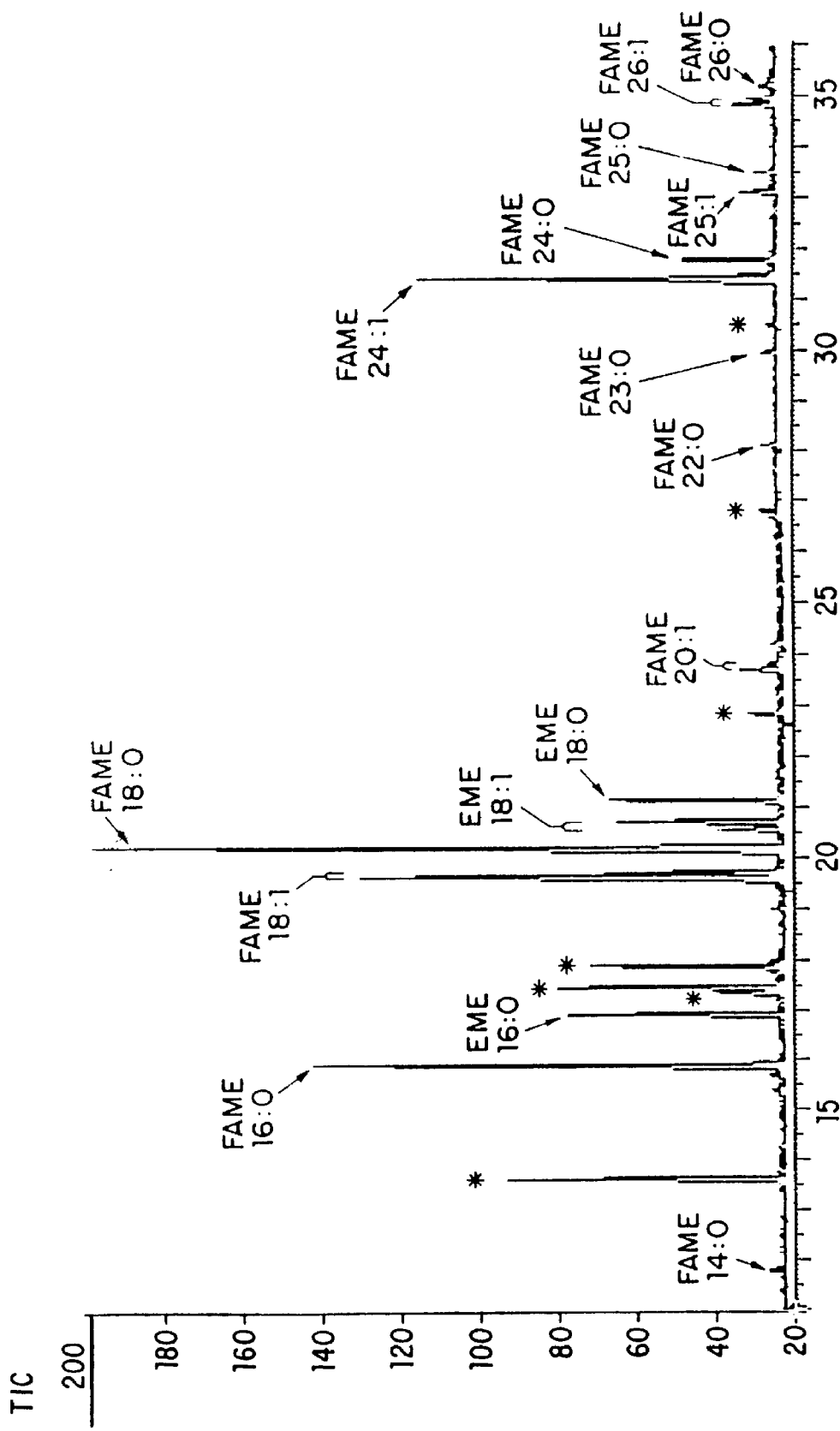
FIG. 13 is a gas chromatography-electron impact/mass spectrometry (GC-EI/MS) pattern of long chain fatty acid methyl esters (FAME's) and enol methyl ethers (EME's) from methanolysis of unknown lipid component: The peaks were identified as marked. Peaks marked by an asterisk are unidentified impurities.

FIG. 13 is a CG-EI/MS of long chain FAMEs and EMEs from methanolysis of the unknown lipid component. The peaks were identified as marked. Peaks marked by an asterisk are unidentified impurities.

Figure 14:
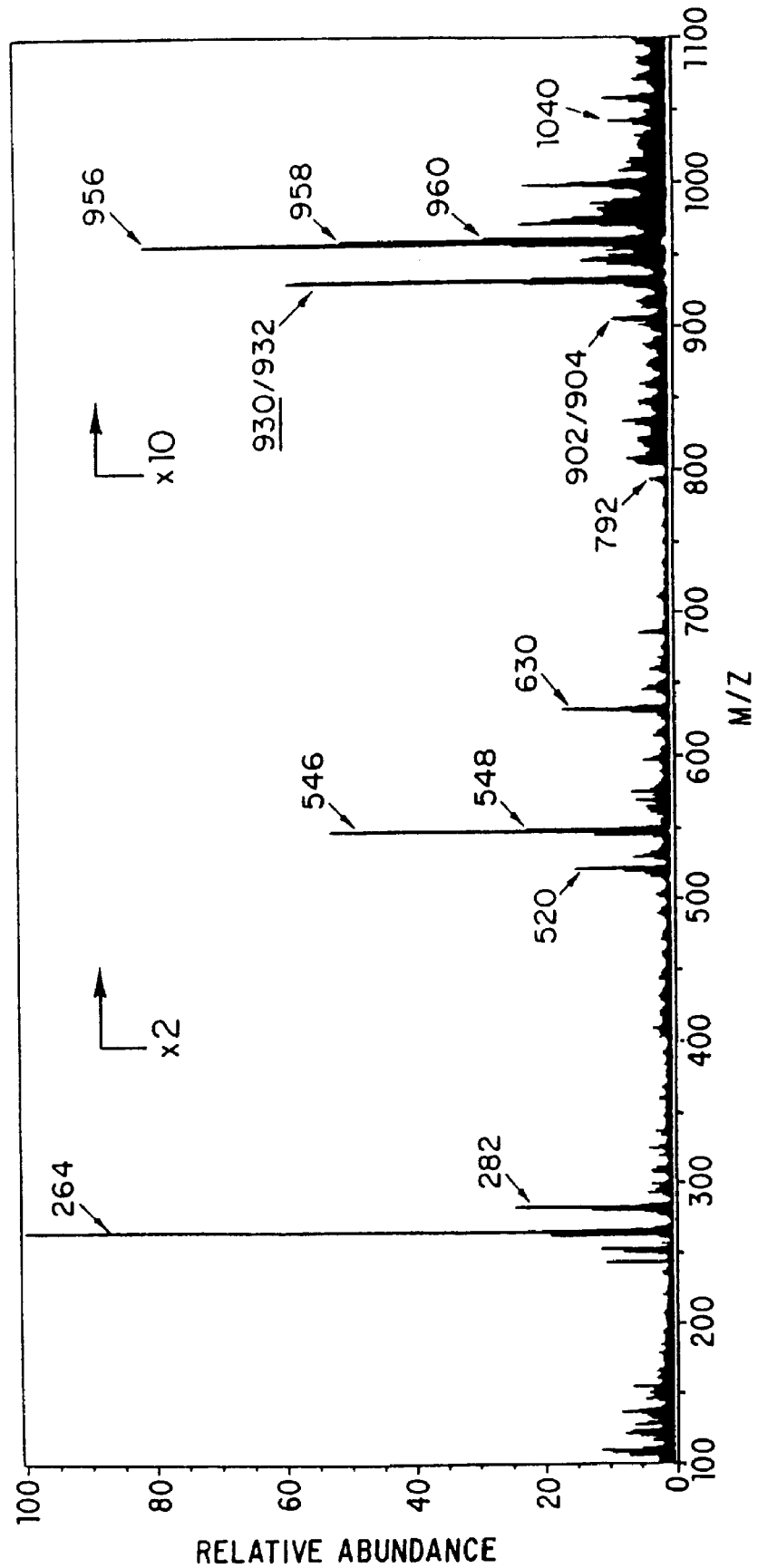
FIG. 14 is a positive ion fast atom bombardment (+FAB) mass spectrum of unknown lipid component in a 3-nitrobenzyl alcohol (NBA) matrix. The peaks are labelled with nominal, monoisotopic masses.

$^+$FAB-MS analysis of native lipid. A FAB mass spectrum of the unknown native lipid was obtained in the positive ion mode. The spectrum is reproduced in FIG. 14. In FIG. 14, the peaks are labeled with nominal, monoisotopic masses.

The spectrum was characterized in the lower mass end by fragments at m/z 282 and 264, which correspond in both mass and relative abundance to the sphingosine-related ions derived by de-N-acylation and dehydration of ceramide (W' and W", respectively, in the nomenclature of Domon and Costello (35), as commonly found in positive ion FAB and FAB-CID (fast atom bombardment-collision induced dissociation) spectra of cerebrosides having d18:1 sphingosine (36, 38, 41). Ceramide ions ($Y_0$) were found most abundantly at m/z 520, 546, 548, and 630, corresponding to compositions having d18:1 sphingosine N-acylated primarily with 16:0, 18:1, 18:0, and 24:1 fatty acids. These would be expected on the basis of the FAME analysis (FIG. 13). A small peak consistent with a cerebroside [MH]$^+$ was observed at m/z 792 (corresponding to Hex.Cer with d18:1 sphingosine and 24:1 fatty acid). The primary group of psuedomolecular ions [MH]$^+$ were found at m/z 930, 932, 956, 958, and 960. The even mass numbers observed correspond to odd molecular weights, and therefore to compounds containing an odd number of nitrogen atoms. In analogy to the psychosine acetal structures determined previously, these pseudomolecular ion species were hypothesized to correspond to cerebrosides which have been modified by long chain fatty aldehydes attached in cyclic acetal linkages to vicinal hydroxy groups of the galactose moiety. As determined by analysis of the GC-MS peaks corresponding to long-chain EME's (FIG. 13), these aldehydes would be primarily 16:0, 18:1, and 18:0 species. The observed pseudomolecular ion abundances would therefore reflect a complex distribution according to the proportions of both fatty acid and fatty aldehyde moieties of different lengths found in the lipid. For example, the most abundant pseudomolecular ion at m/z 956 would correspond to a galactocerebroside acetal having d18:1 sphingosine, 18:1 fatty acid and 18:1 fatty aldehyde. The ion at m/z 930 could correspond to either d18:1 sphingosine, 18:1 fatty acid, and 16:0 aldehyde, or d18:1 sphingosine, 16:0 fatty acid, and 18:1 aldehyde. Other ions in the cluster represent other possible combinations (all with d18:1 sphingosine) of the most abundant fatty acid and aldehyde species. The conclusion that the compounds are cerebrosides modified by acetal linkage to vicinal hydroxy groups of galactose was confirmed by methylation/linkage analysis, as described below.

Methylation analysis by GC-MS. Following permethylation, acid hydrolysis, reduction, and acetylation of the native lipid, the resulting partially methylated hexitol acetates were analyzed by GC-MS.

Figure 15:
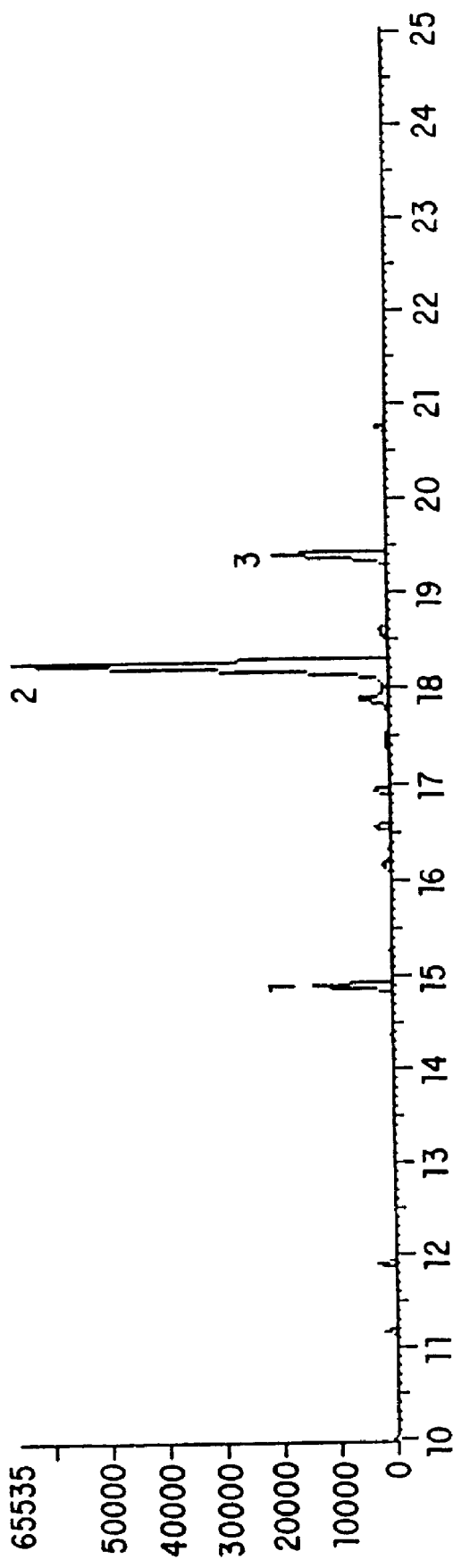
FIG. 15 is a gas chromatography-mass spectrometry (GC-MS) analysis of partially methylated alditol acetates (PMAA's) from permethylation, hydrolysis, reduction and acetylation of unknown lipid component. Peaks are identified as PMAAs of 1: 2,3,4,6-tetra-O-; 2: 2,6-di-O-; and 3: 4,6-di-O-Me-Gal.

The results are shown in FIG. 15.

In FIG. 15, the peaks are identified as PMAAs of 1: 2,3,4,6-tetra-O-; 2: 2,6-di-O-; and 3: 4,6-di-O-Me-Gal.

The primary component detected was 2,6-di-O-Me-Gal, along with smaller peaks corresponding to 2,3-di-O-Me-Gal and 2,3,4,6-tetra-O-Me-Gal. The di-O-Me- peaks represent 3,4- and 4,6-linked substituents, respectively, on galactose and show that the lipid fraction must be comprised of isomeric cyclic acetals derived from cerebroside, mostly in a five-membered 3,4-linked ring, with some six-membered 4,6-linked ring. The small trace of 2,3,4,6-tetra-O-Me-Gal is consistent with the low abundance pseudo-molecular ion detected for unsubstituted cerebroside. These linkages were also found in separate components of the psychosine acetals previously determined. The chiralities of the acetal C-1 positions have not been definitively determined. However, they are believed to be an equatorial orientation for the long chain in the six-membered acetal ring, and a pseudo-equatorial orientation for this group in the five-membered ring is assumed.

EXAMPLE 8

DETERMINATION OF NEURITOGENIC ACTIVITY

Neuritogenic activity of compounds A, B, C, D and E was determined as previously described (10), employing various neuroblastoma cell lines in which neurite formation is dependent either on nerve growth factor (NGF) or ganglioside. Neuroblastoma cell lines were cultured in gelatin-coated plates as described previously (11,12). Various concentrations (5–150 $\mu$M) of glycolipid were added and cultured for observation of neurite formation. Incidence of cells forming neurites >50 $\mu$m long was counted as a percent of total population. Photographs for cells treated with compounds A and B were taken at 24 hour intervals.

Striking neurite formation was observed in mouse neuroblastoma Neuro-2A cells on addition of plasmalopsychosine compounds A and B, particularly in the presence of NGF at 50 $\mu$g/ml concentration; neurites, i.e., >50 $\mu$m long, comprised as much as 60–80% of the total cell population. This concentration was much lower than that previously reported for a ganglioside effect. That is, the most effective ganglioside, GT1b, required a concentration of 200 $\mu$g/ml. A mixture of bovine brain ganglioside required at least 100–150 $\mu$g/ml. Other types of cells, including mouse and human neuroblastoma, showed similar degrees of neuritogenesis induced by plasmalopsychosine. Psychosine by itself showed a strong cytotoxic effect on various neuroblastoma cell lines; cell growth was inhibited, morphology changed, and cells eventually died in the presence of 10–20 $\mu$g/ml psychosine. No neuritogenesis occurred in the presence of psychosine. Patterns of neurite formation for plasmalopsychosine compounds A and B are shown in FIGS. 9A, 9B and 10.

Figure 9A:
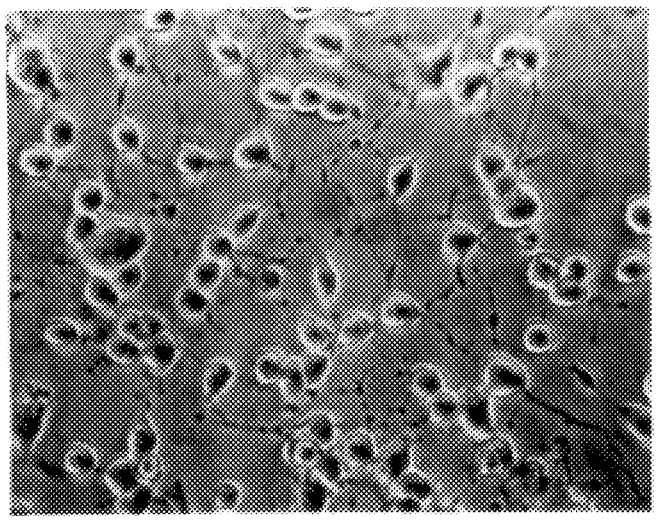
FIGS. 9A and 9B are neuritogenesis patterns of Neuro-2A cells in the presence of 50 $\mu$g/ml plasmalopsychosine.
Figure 9B:
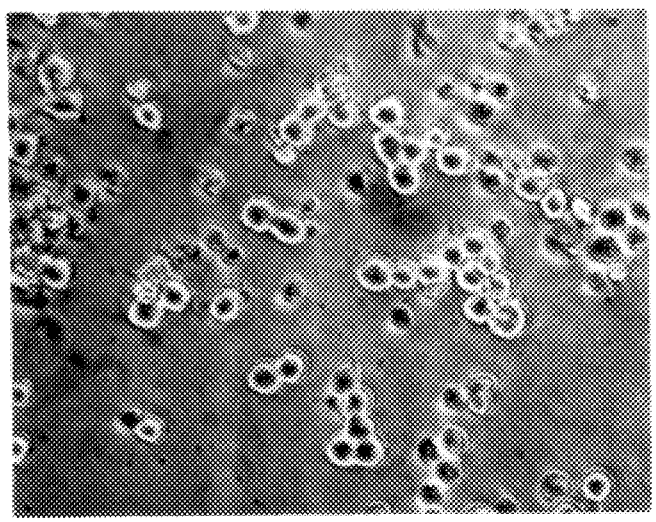

FIGS. 9A and 9B show a neuritogenesis pattern of Neuro-2A cells in the presence of 50 $\mu$g/ml plasmalopsychosine compounds A and B at different areas on the culture dish.

Figure 10:
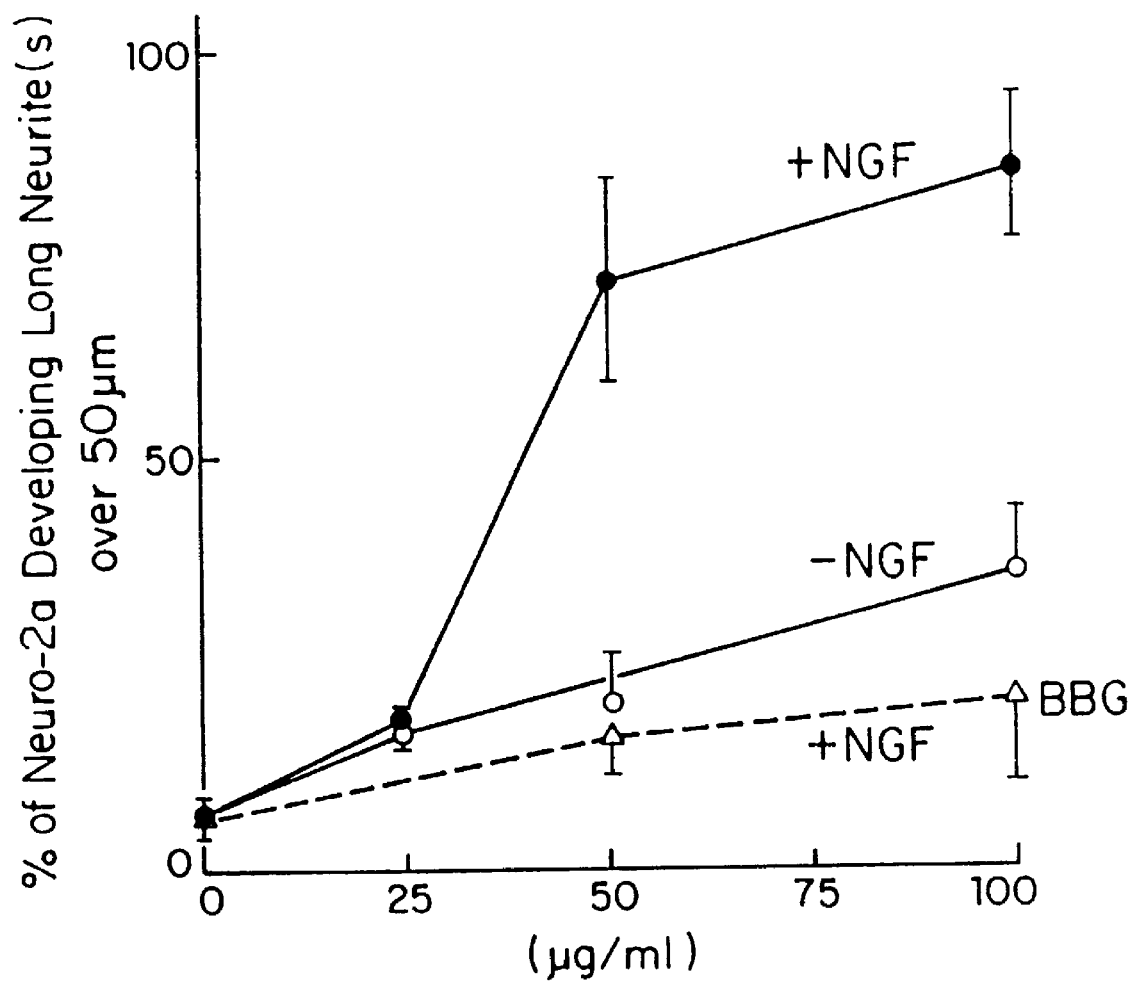
FIG. 10 is a graph showing the effect of plasmalopsychosine on neurite formation in Neuro-2A cells: Abscissa: concentration of plasmalopsychosine ($\mu$g/ml). Ordinate: percentage of Neuro-2A cells developing neurites (>50 $\mu$m in length). The circles (open and closed) represent results for a mixture of the upper and middle bands of plasmalopsychosine, + and − nerve growth factor (NGF); the open triangles represent results in the presence of NGF for a mixture of bovine brain gangliosides (BBG) containing the gangliosides GM1, GD1a, GD1b and GT.

FIG. 10 is a graph showing the effect of plasmalopsychosine on neurite formation in Neuro-2A cells, wherein the abscissa represents the concentration of plasmalopsychosine ($\mu$g/ml) and the ordinate represents the percentage of Neuro-2A cells developing neurites (>50 $\mu$m in length). The circles (open and closed) represent results for a mixture of the upper and middle bands of plasmolopsychosine, + and − nerve growth factor (NGF). The open triangles represent results in the presence of NGF for a mixture of bovine brain gangliosides (BBG) containing the gangliosides GM1, GD1a, GD1b and GT.

The results represented in FIG. 10 show that even when NGF is added to cells treated with plasmolopsychosine, no effect is seen. Thus, the neurite formation is due to the plasmalopsychosine.

Plasmalocerebroside had no clear effect in early stages of cell culture. However, neurite formation, i.e., >50 $\mu$m long, became increasingly apparent by 1 week. Thus, plasmalocerebroside possesses neuritogenic activity. With 50 $\mu$g/ml concentration, after 2 weeks of incubation, neurite formation in Neuro-2A cell culture was more pronounced in the presence of plasmalocerebroside than plasmalopsychosine.

EXAMPLE 9

CHEMICAL SYNTHESIS OF COMPOUNDS A AND B

Figure 16:
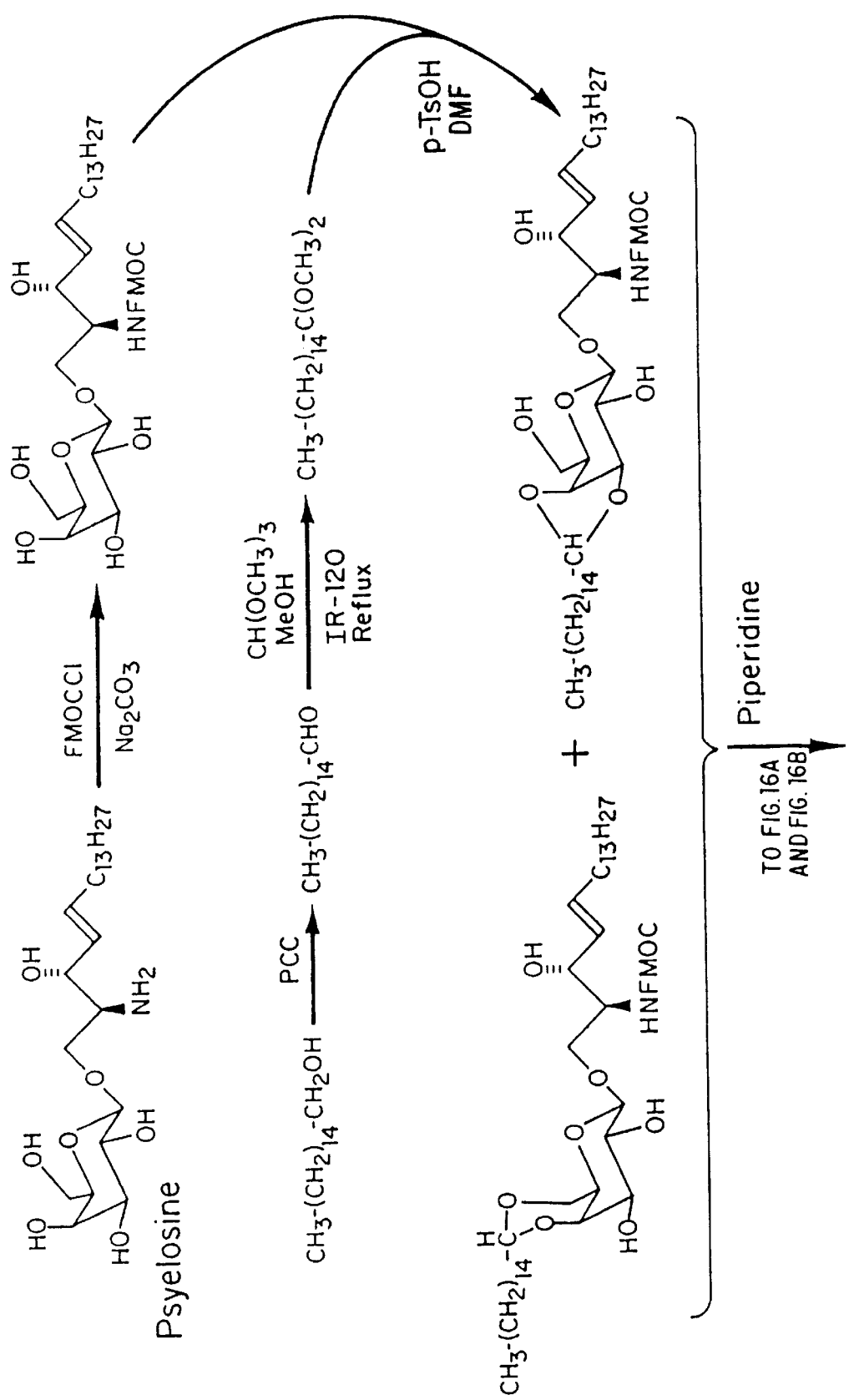
FIGS. 16, 16A, and 16B shows a scheme for synthesizing plasmalopsychosine compounds A and B.
Figures 16A, 16B:
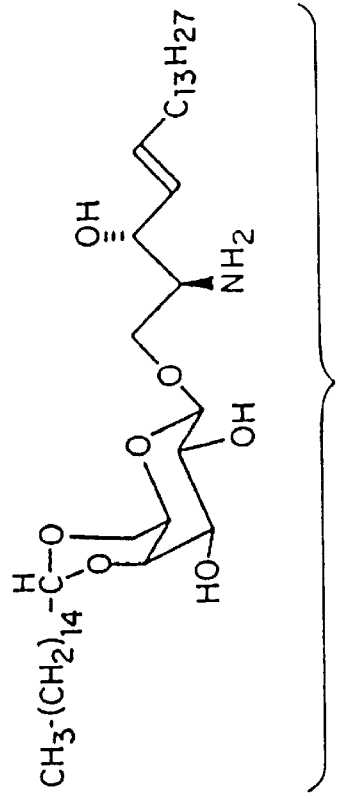

Plasmalopsychosine A and B were chemically synthesized from psychosine according to the "Synthetic scheme for plasmalopsychosine A and B" (FIG. 16).

To a solution of psychosine (prepared synthetically or obtained by the alkaline hydrolysis of CMH extracted from bovine brain) in a mixture of chloroform and water, 9-fluorenylmethyl chloroformate and potassium carbonate (45) were added and the reaction mixture was stirred at room temperature for 21 hours. After the evaporation of the reaction mixture in vacuo, a small volume of water was added to the residue which formed a white slurry. This slurry was loaded on a pre-conditioned BOND ELUT C-18 column and rinsed with water ro remove water-soluble components. The retained lipophilic compounds were recovered by eluting the column with methanol and the eluate was evaporated in vacuo to give FMOC-psychosine. Thin layer chromatography of the product in chloroform/methanol 9:1 or toluene/methanol 3:1 showed the presence of some U.V. positive impurities, which were removed using a silica column and toluene/methanol 3:1 or chloroform/methanol 9:1 as solvent mixture. The purified compound, obtained in 87% yield, $[\alpha]^{25}_D$+5.17 (C 1.42 in CHCl$_3$) was then used for making cyclic acetals of psychosine.

The other reactant,α-α-dimethoxy hexadecane, required for the formation of cyclic acetals was synthesized in two steps from n-hexadecanol (Aldrich, Milwaukee, Wis.): i) Oxidation using pyridinium chlorochromate (46) in dichloromethane to give aldehyde and ii) reaction of the aldehyde with trimethylorthoformate (Aldrich, Milwaukee, Wis.) in the presence of AMBERLITE IR-120 (Rohm & Haas Co., Pa.) under reflux (47).

Cyclic acetals were prepared as follows: To a solution of FMOC-psychosine in N,N-dimethylformamide, α-α-dimethoxy hexadecane and p-toluene sulfonic acid were added and the reaction mixture was stirred at room temperature for 19 hours. Then the reaction mixture was quenched with triethylamine to neutralize p-toluene sulfonic acid, and evaporated in vacuo. Residue was transferred to a BOND ELUT C-18 column and rinsed with water. Cyclic acetals of FMOC-psychosine along with other lipophilic compounds were finally eluted from the column using methanol, and eluate was evaporated in vacuo. Desired cyclic acetals were roughly separated from other compounds by silica column chromatography using toluene/methanol 3:1 solvent.

The mixture of cyclic acetals of FMOC-psychosine was then treated with pipyridine for three hours to remove FMOC protecting group (48), and evaporated in vacuo.

Separation of plasmalopsychosine A and B from other products was accomplished using isopropanol/hexane/water gradient on IATROBEADS (10 $\mu$M) column, pre-equilibrated as described in Example 1.

Figure 17:
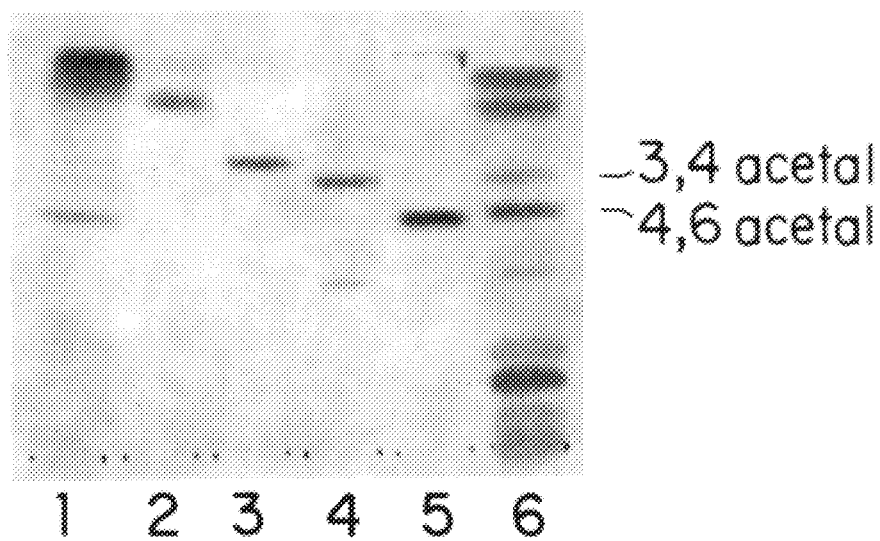
FIG. 17 is a HPTLC pattern of fractions obtained on an IATROBEADS column of the plasmalopsychosine synthetic products (Lanes 2–5) compared with crude synthetic product (Lane 1) and anionic lipids obtained from CM-sephadex column chromatography of human brain extract (Lane 6). The HPTLC was developed in chloroform/methanol/28% $NH_4OH$ (80:20:2) and visualized by spraying with orcinal-sulfuric acid and baking on a hot plate.

The sample was prepared for injection by adding 100$\mu$l of chloroform/methanol 2:1 and slightly warming while sonicating. To this about 1.5 ml of hexane was added during sonication. Sample was loaded onto the column and eluted with hexane, gradually changing to isopropanol/hexane/water gradient 30:69:1 over a period of 200 minutes and eluting with same gradient for 50 minutes (200–250 minutes). Gradient was finally changed to 55:25:20 (250–400 minutes) and elution was continued for the next 200 minutes (400–600 minutes) with the same gradient. Eluate (6 mins/tube) was collected and each fraction was checked by HPTLC (chloroform/methanol/NH$_4$OH 80:20:2). Identical fractions on HPTLC were pooled together, concentrated and compared with anionic lipid fractions of human brain obtained from carboxymethyl sephadex column chromatography. The results are shown in FIG. 17, where Lane 1 is crude synthetic preparation of psychosine acetals, Lanes 2–5 are pooled fractions of synthetic product from HPLC on an IATROBEAD column, and Lane 6 is total eluate of anionic lipid fractions of human brain (cerebrum) obtained from carboxymethyl sephadex column with 0.5M triethylamine.

Figure 18A:
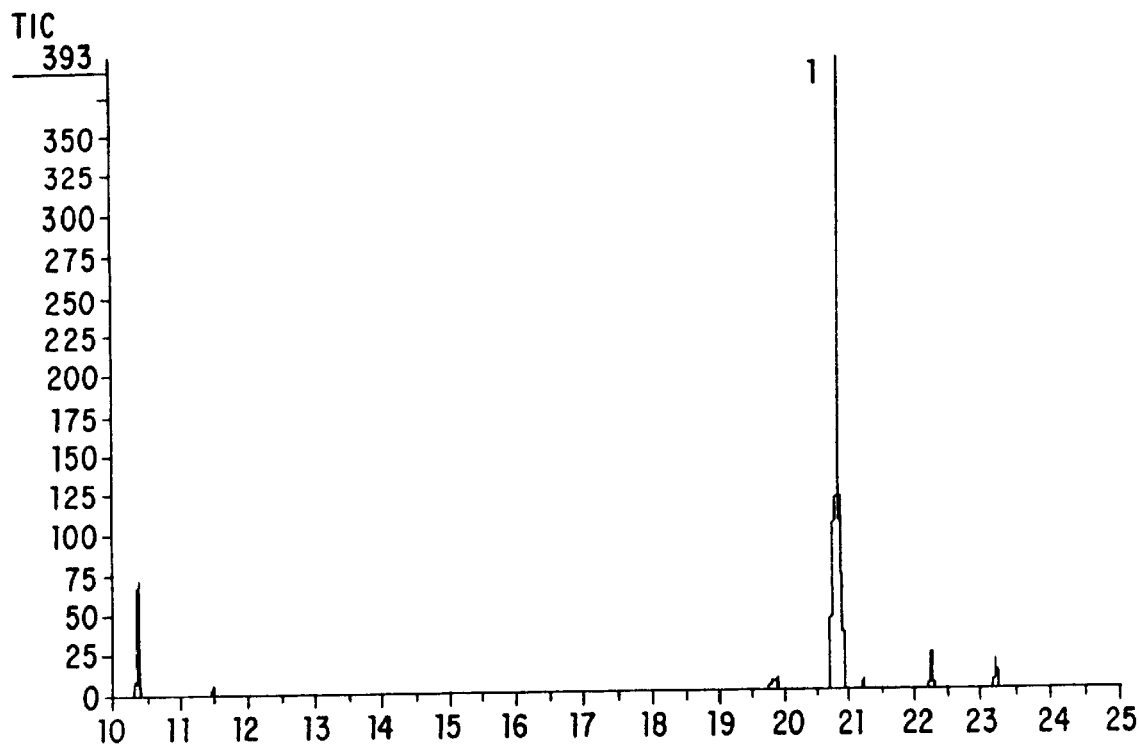
FIGS. 18A–18C are data from GS-MS analysis of partially methylated alditols/acetals from permethylation, hydrolysis, reduction and acetylation of the plasmalopsychosine synthetic products.
Figure 18B:
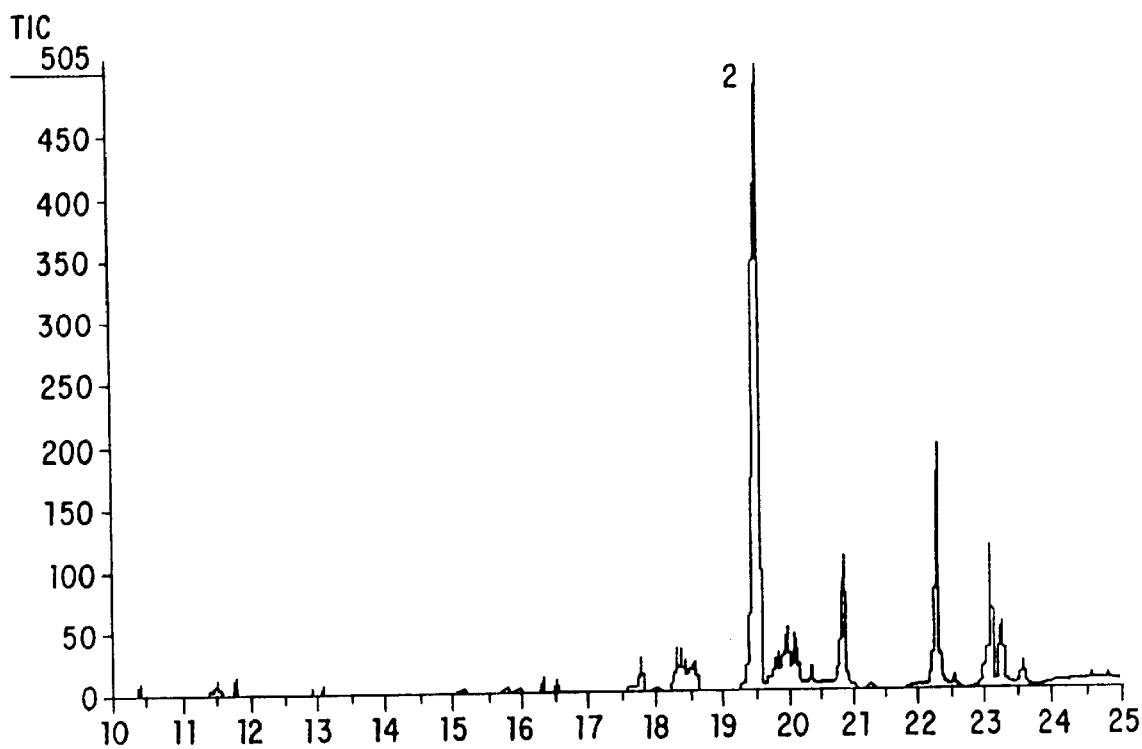
Figure 18C:
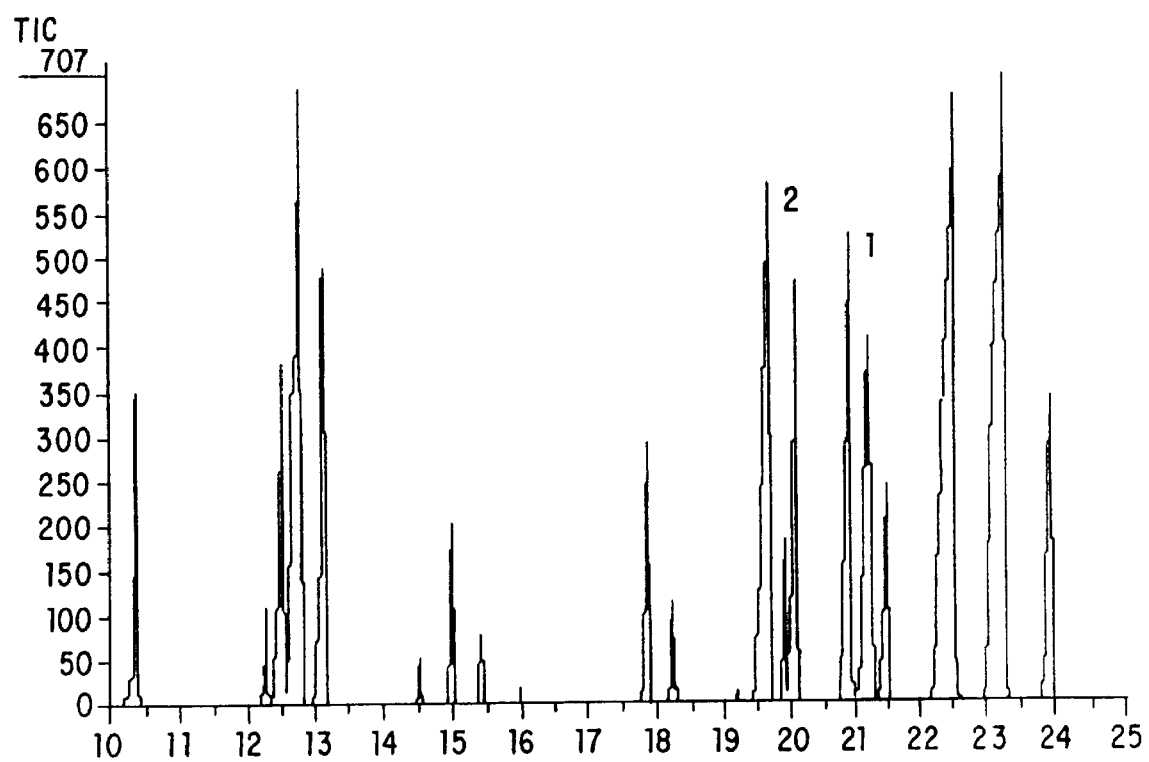

Fractions identical to upper and middle band lipids plasmalopsychosine A and plasmalopsychosine B were further characterized by NMR, FAB-MS and methylation by GC-MS (FIGS. 18A–18C), which conformed to the assigned structure. Fractions of Lane 2 and Lane 3 of FIG. 17 have not yet been characterized.

REFERENCES

1. Hannun, Y. A. and R. M. Bell (1987) *Science* 235, 670–674.
2. Hannun, Y. A. and R. M. Bell (1989) *Science* 243, 500–507.
3. Hakomori, S. (1990) *J. Biol. Chem.* 265, 18713–18716.
4. Igarashi, Y. (1990) *Trends Glycosci. Glycotechnol.* 2, 319–332.
5. Folch-Pi, J., S. Arsove, and J. A. Meath (1951) *J. Biol. Chem.* 191, 819–831.
6. Feulgen, R., K. Imhäuser, and M. Behrens (1929) *Hoope-Seyler's Z. Physiol. Chem.* 2, 161–180.
7. Kannagi, R., S. B. Levery, and S. Hakomori (1985) *J. Biol. Chem.* 260, 6410–6415.
8. Kannagi, R., S. B. Levery, and S. Hakomori (1984) *J. Biol. Chem.* 259, 8444–8451.
9. Kannagi, R., S. B. Levery, F. Ishigami, S. Hakomori, L. H. Shevinsky, B. B. Knowles, and D. Solter (1983) *J. Biol. Chem.* 258, 8934–8942.
10. Ledeen, R. W., G. Wu, K. K. Vaswani, and M. S. Cannella, (1990) in *Trophic factors and the nervous system* (Horrocks, L. A., Neff, N. H., Yates, A. J., and Hadjiconstantinou, M., eds.), pp. 17–34. Raven Press, New York, N.Y.
11. Cannella, M. S., F. J. Roisen, T. Ogawa, M. Sugimoto, and R. W. Ledeen (1988) *Dev. Brain Res.* 39, 137–143.
12. Cannella, M. S., A. J. Acher, and R. W. Ledeen (1988) *Int. J. Dev. Neurosci.* 6, 319–326.
13. Kochetkov, N. K., I. G. Zhukova, and I. S. Glukhoded (1963) *Biochim. Biophys. Acta* 70, 716–719.
14. Wittenberg, J. B., S. R. Korey, and F. H. Swenson (1956) *J. Biol. Chem.* 219, 39–47.
15. Klenk, E., and J. P. Lohr (1967) *Z. Physiol. Chem.* 348, 1712.
16. Tamai, Y. (1968) *Jap. J. Exp. Med.* 38, 65.
17. Tamai, Y., T. Taketomi, and T. Yamakawa (1967) *Jap. J. Exp. Med.* 37, 79.
18. Kishimoto, Y., M. Wajda, and N. S. Radin (1968) *J. Lipid Res.* 9, 27–33.
19. Feulgen, R., and K. Voit (1924) *Pflügers Arch.* 206, 389.
20. Klenk, E., and H. Debuch (1963) *Chem. Phys. Lipids* 6, 1–29.
21. Hakomori, S., T. Ishimoda, H. Kawauchi, and F. Eidoh (19–61) *J. Biochem. (Tokyo)* 49, 307–316.
22. Levery, S. B. and S. Hakomori (1987) *Meth. Enzymol.* 138, 13–25.
23. Ballou, C. E. and A. Dell (1985) *Carboh. Res.* 140, 139–143.
24. Hara, A. and T. Taketomi (1986) *J. Biochem.* 100, 415–423.
25. Corey, E. J., and G. Schmidt (1979) *Tetrahedron. Lett.* 399–402.
26. Sweeley, C. C., R. Bentley, M. Makita, and W. W. Wells (1963) *J. Am. Chem. Soc.* 85, 2497–2507.
27. Laine, R. A., W. J. Esselman, and C. C. Sweeley (1963) *Methods Enzymol.* 28, 159–167.
28. Ciukanu I., and K. Kerek (1984) *Carbohydr. Res.* 131, 209–217.
29. Larson, G., H. Karisson, G. C. Hanson, and W. Pimlott (1987) *Carbohydr. Res.* 161, 281–290.
30. Zemplén, G., (1927) *Ber.* 60:1555–1557.
31. Bjørndal, H., C. G. Hellerqvist, B. Lindberg, and S. Svensson (1970) *Angew. Chem. Intl. Ed. Engl.* 9:610–619.
32. Jansson, P. E., L. Kenne, H. Lindgren, B. Lindberg and J. Lönngren (1976) *Chem Commun. Univ. Stockholm.* 8, 1–74.
33. Holmes, E. H., and S. B. Levery, (1989) *Arch. Biochem. Biophys.* 274, 14–25.
34. Holmes, E. H., and S. B. Levery (1989) *Arch. Biochem. Biophys.* 274, 663–647.
35. Domon, D. and C. E. Costello (1988) *Glycoconi. J.* 5, 397–409.
36. Domon, D. and C. E. Costello (1988) *Biochem.* 27, 1534–1543.
37. Feulgen, R. and Grünberg, H. (1938–1939) *Z. Physiol. Chem.* 257, 161.
38. Hemling, H. E., Yu, R. K., Sedjwick D. and Rinehart Jr., K. L. (1984) *Biochem.* 23, 5706–5713.
39. Kochetkov, N. K., Zhukova, I. G. & Glukhoded, I. S. (1962) *Biochim. Biophys. Acta* 60, 431.
40. Norton, W. T. & Brotz, M. (1963) *Biochem. Biophys. Res. Commun.* 12, 198.
41. Ohashi, Iwamori, Y., N., Ogawa, T., and Nagai, Y., (1987) *Biochem.* 26, 3990–3995.
42. Tamai, Y. (1968), *Japanese J. Exp. Med.* 33(1), 65–73.
43. Kubota, M. and T. Taketomi (1974) *Japanese J. Exp. Med.* 44(2), 145–150.
44. Klenk, E. and M. Doss (1966) *Hoope-Seyler's Zs Physiol.* 346, 296–298.
45. Carpino, L. A. and G. Y. Han (1972) *J. Org. Chem.* 37, 3404.
46. Corry, E. J. and J. W. Suggs (1975) *Tetrahedron Letters* 2647.
47. Evens, M. E. (1972) *Carbohydrate Res.* 41, 473.
48. Godansky, M., S. S. Deshmane and J. Martinez (1979) *J. Org. Chem.* 44, 1622.

While the invention has been described in detail above with reference to a preferred embodiment, various modifications within the scope and spirit of the invention will be apparent to people of working skill in this technological field. Thus, the invention should be considered as limited only by the scope of the appended claims.

What is claimed is:

1. A method of forming neurites from nerve cells comprising contacting said cells with an effective amount of one or more plasmalopsychosine and/or plasmalocerebrosides selected from the group consisting of compound A, compound B, compound C and compound D:

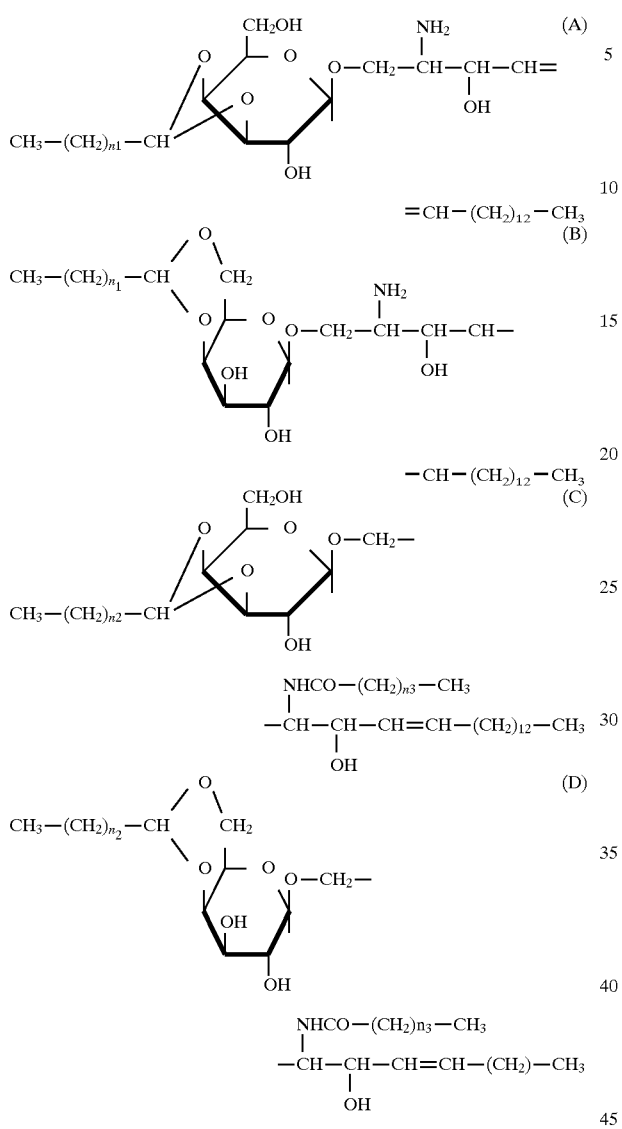

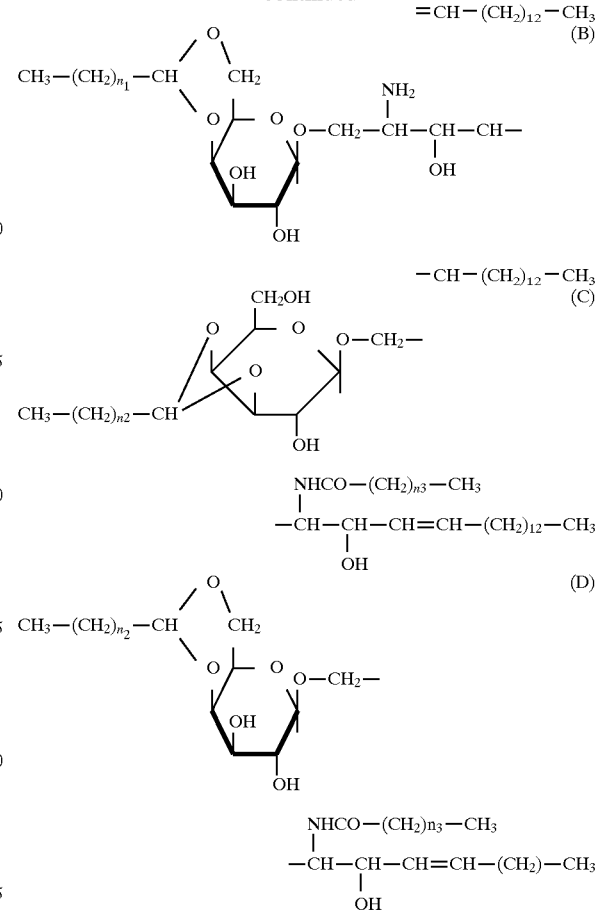

wherein $n_1$, $n_2$ and $n_3$ each is 0–50.

2. A method for treating neuronal diseases and/or neuronal tissue damage comprising administering to a host in need of such treatment a therapeutically effective amount of one or more plasmalopsychosine and/or plasmalocerebrosides selected from the group consisting of compound A, compound B, compound C and compound D:

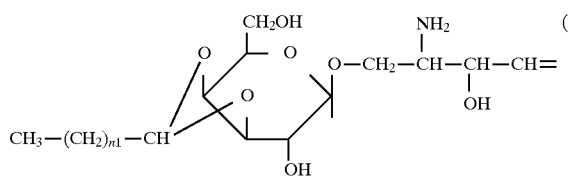

wherein $n_1$, $n_2$ and $n_3$ each is 0–50; and biologically compatible salts thereof.

3. The method of claim 1, wherein said one or more plasmalopsychosine and/or plasmalocerebrosides comprises compound A or compound B.

4. The method of claim 1, wherein said one or more plasmalopsychosine and/or plasmalocerebrosides comprises compound A.

5. The method of claim 1, wherein said one or more plasmalopsychosine and/or plasmalocerebrosides comprises compound C or compound D.

6. The method of claim 1, further comprising contacting said cells with nerve growth factor.

7. The method of claim 2, wherein said one or more plasmalopsychosine and/or plasmalocerebrosides comprises compound A or compound B.

8. The method of claim 2, wherein said one or more plasmalopsychosine and/or plasmalocerebrosides comprises compound A.

9. The method of claim 2, wherein said one or more plasmalopsychosine and/or plasmalocerebrosides comprises compound C or compound D.

10. The method of claim 2, further comprising administering a therapeutically effective amount of nerve growth factor.

* * * * *